(12) United States Patent
Otani et al.

(10) Patent No.: US 10,199,578 B2
(45) Date of Patent: Feb. 5, 2019

(54) FLUORINE-ATOM-CONTAINING POLYMER AND USE THEREOF

(71) Applicant: NISSAN CHEMICAL INDUSTRIES, LTD., Tokyo (JP)

(72) Inventors: Naoki Otani, Funabashi (JP); Hirofumi Ota, Funabashi (JP)

(73) Assignee: NISSAN CHEMICAL INDUSTRIES, LTD., Tokyo (JP)

( * ) Notice: Subject to any disclaimer, the term of this patent is extended or adjusted under 35 U.S.C. 154(b) by 90 days.

(21) Appl. No.: 15/324,790

(22) PCT Filed: Jul. 10, 2015

(86) PCT No.: PCT/JP2015/069833
§ 371 (c)(1),
(2) Date: Jan. 9, 2017

(87) PCT Pub. No.: WO2016/006674
PCT Pub. Date: Jan. 14, 2016

(65) Prior Publication Data
US 2017/0200897 A1    Jul. 13, 2017

(30) Foreign Application Priority Data

Jul. 10, 2014 (JP) .................. 2014-141942
Mar. 31, 2015 (JP) .................. 2015-073227

(51) Int. Cl.
*H01L 51/00* (2006.01)
*H01L 51/42* (2006.01)
*C07C 209/00* (2006.01)
*C07C 211/56* (2006.01)
*C08G 61/12* (2006.01)
(Continued)

(52) U.S. Cl.
CPC ........ *H01L 51/0039* (2013.01); *C07C 211/56* (2013.01); *C08G 61/12* (2013.01); *C08G 61/121* (2013.01); *C09D 5/24* (2013.01); *C09D 7/61* (2018.01); *C09D 7/63* (2018.01); *C09D 165/00* (2013.01); *H01L 51/0043* (2013.01); *H01L 51/0059* (2013.01); *H01L 51/50* (2013.01); *H05B 33/10* (2013.01); *C08G 2261/124* (2013.01); *C08G 2261/1424* (2013.01); *C08G 2261/3142* (2013.01); *C08G 2261/3162* (2013.01); *C08G 2261/411* (2013.01); *C08G 2261/51* (2013.01); *C08G 2261/95* (2013.01); *C08K 3/32* (2013.01); *C08K 5/18* (2013.01);
(Continued)

(58) Field of Classification Search
CPC ... H01L 51/00; H01L 51/002; H01L 51/0042; H01L 51/0059; H01L 51/0081; H01L 51/5048; H01L 51/5088; H01L 51/5092; C07C 209/06; C07C 211/54
See application file for complete search history.

(56) References Cited

U.S. PATENT DOCUMENTS

2005/0227465 A1    10/2005  Smith et al.

FOREIGN PATENT DOCUMENTS

JP    5-239454 A      8/2006
JP    2006-225590 A   8/2006
(Continued)

OTHER PUBLICATIONS

Adachi et al., "Electroluminescence in Organic Films with Three-Layer Structure", Japanese Journal of Applied Physics, vol. 27, No. 2, Feb. 1988, pp. L269-L271.
(Continued)

*Primary Examiner* — Haidung D Nguyen
(74) *Attorney, Agent, or Firm* — Birch, Stewart, Kolasch & Birch, LLP

(57) ABSTRACT

Provided are a fluorine-atom-containing polymer that is a condensation polymer of a fluorine-atom-containing triphenylamine derivative giving a repeating unit represented by formula (1) and a fluorine derivative giving a repeating unit represented by formula (2) and the use of this fluorine-atom-containing polymer.

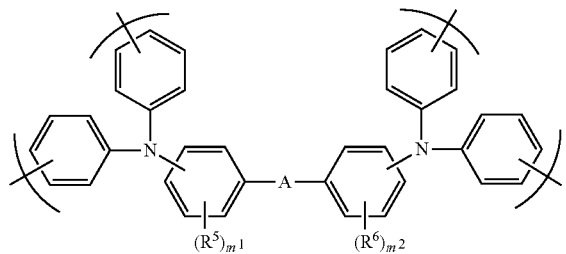

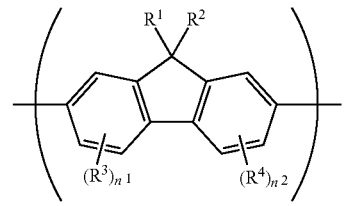

(In the formulas, A represents a fluoroalkanediyl group, at least one of $R^1$ and $R^2$ represents any of an alkoxyl group, an alkenyloxy group, an alkynyloxy group, an aryloxy group, a heteroaryloxy group, and an alkyl group including at least one ether structure, $R^3$-$R^6$ represent prescribed substituents, $m^1$ and $m^2$ each independently represent an integer of 0-4, $n^1$ and $n^2$ represent an integer of 0-3.)

11 Claims, 1 Drawing Sheet

(51) Int. Cl.
  *H01L 51/50*      (2006.01)
  *H05B 33/10*      (2006.01)
  *C09D 7/61*       (2018.01)
  *C09D 7/63*       (2018.01)
  *C09D 5/24*       (2006.01)
  *C09D 165/00*     (2006.01)
  *C08K 3/32*       (2006.01)
  *C08K 5/18*       (2006.01)
  *C08K 5/3445*     (2006.01)

(52) U.S. Cl.
  CPC ...... *C08K 5/3445* (2013.01); *C08K 2003/329* (2013.01); *H01L 51/5056* (2013.01); *Y02E 10/549* (2013.01); *Y02P 70/521* (2015.11)

(56) References Cited

FOREIGN PATENT DOCUMENTS

| | | |
|---|---|---|
| JP | 2007-531762 A | 11/2007 |
| JP | 2013-256655 A | 12/2013 |

OTHER PUBLICATIONS

Chen et al., "Light-Emitting Organic Materials with Variable Change Injection and Transport Properties", Chem. Mater., vol. 18, 2006, pp. 204-213.
International Search Report (PCT/ISA/210) issued in PCT/JP2015/069833, dated Oct. 13, 2015.
Written Opinion (PCT/ISA/237) issued in PCT/JP2015/069833, dated Oct. 13, 2015.

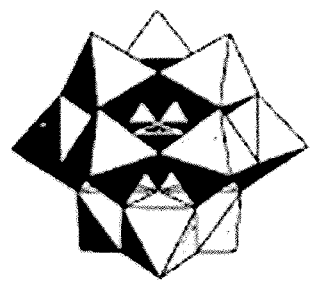
(A1)
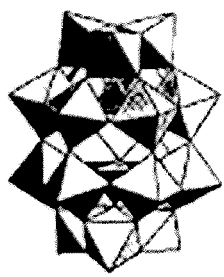
(A2)

FLUORINE-ATOM-CONTAINING POLYMER AND USE THEREOF

TECHNICAL FIELD

The present invention relates to fluorine-atom-containing polymers and use thereof.

BACKGROUND ART

In organic electroluminescent (EL) elements, a charge-transporting thin film is used. Methods for forming the charge-transporting thin film are generally classified into dry process typified by the vapor deposition method and wet process represented by the spin coating method. These methods are appropriately used selectively, according to the area of the thin film to be formed and the solubility of the substance to be formed into the thin film in organic solvents.

In general, a layer called a hole injection layer and a layer called a hole transport layer are disposed between an anode and a light-emitting layer of an organic EL element, in this order from the anode side. The provision of these two layers makes it possible to enable efficient charge transfer, and to obtain an organic EL element which has high luminance characteristics (see, for example, Non-Patent Document 1). On the other hand, however, in the organic EL element production process, normally, there is a drawback that independent steps for forming each of these layers are needed.

In the field of electronic devices in recent years, simplification of process and simplification of element structure have been demanded, for the purpose of producing the elements in high yield and efficiently. Particularly, when a functional multilayer film in which a plurality of layers in an element are formed in a multilayer form is replaced by a single film, not only the production process can be simplified but also the element structure can be directly simplified. In view of this, in the field of various electronic devices, there is a demand for a material from which a functional single film capable of substituting an existing functional multilayer film can be produced. In the field of organic EL, also, there has been an increasing demand for a material which enables conversion of a functional multilayer film, composed of a hole injection layer and a hole transport layer as in a general structure, into a single film.

PRIOR ART DOCUMENT

Non-Patent Document

Non-Patent Document 1: Adachi C. et al., Jpn. J. Appl. Phys., 1988, 27(2), pp. L269-271

SUMMARY OF THE INVENTION

Problems to be Solved by the Invention

The present invention has been made in consideration of the above-mentioned circumstances. It is an object of the present invention to provide a material for forming a thin film which enables realization of an organic EL element having excellent luminance characteristics, even when used as a single layer between and in contact with an anode and a light-emitting layer.

Means for Solving the Problems

In order to achieve the above object, the present inventors made extensive and intensive investigations. As a result of their investigations, the inventors found out that a predetermined fluorine-atom-containing polymer is excellent in solubility in organic solvents, and that a thin film obtained from a charge transporting varnish containing a charge-transporting substance composed of the fluorine-atom-containing polymer, a fluorine-atom-free charge-transporting substance, a dopant composed of a heteropoly-acid, and an organic solvent gives an organic EL element having excellent luminance characteristics, even in the case where the thin film is used between and in contact with an anode and a light-emitting layer. Based on the finding, the inventors have completed the present invention.

Specifically, the present invention provides the following fluorine-atom-containing polymers and use thereof.

1. A fluorine-atom-containing polymer that is a condensation polymer of a fluorine-atom-containing triphenylamine derivative giving a repeating unit represented by formula (1) and a fluorene derivative giving a repeating unit represented by formula (2):

[Chemical Formula 1]

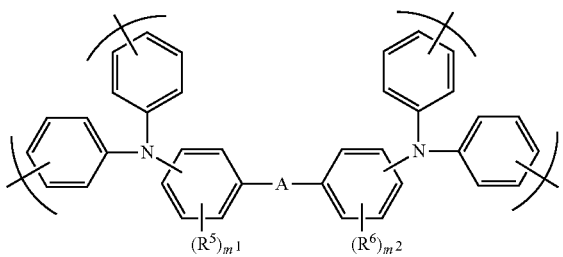

(1)

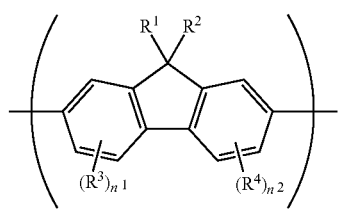

(2)

wherein A represents a $C_1$-$C_6$ fluoroalkanediyl group;

$R^1$ and $R^2$ each independently represent a hydrogen atom, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_2$-$C_{20}$ heteroaryl group, a $C_1$-$C_{20}$ alkoxy group, a $C_2$-$C_{20}$ alkenyloxy group, a $C_1$-$C_{20}$ alkynyloxy group, a $C_6$-$C_{20}$ aryloxy group, a $C_2$-$C_{20}$ heteroaryloxy group, or a $C_2$-$C_{20}$ alkyl group including at least one ether structure (provided that at least one of $R^1$ and $R^2$ represents any of the alkoxy group, the alkenyloxy group, the alkynyloxy group, the aryloxy group, the heteroaryloxy group, and the alkyl group including at least one ether structure);

$R^3$ to $R^6$ each independently represent a halogen atom, a nitro group, a cyano group, a $C_1$-$C_{20}$ alkyl group, a $C_2$-$C_{20}$ alkenyl group, a $C_2$-$C_{20}$ alkynyl group, a $C_1$-$C_{20}$ alkoxy group, a $C_2$-$C_{20}$ alkenyloxy group, or a $C_2$-$C_{20}$ alkynyloxy group that may be substituted with $Z^1$, or a $C_6$-$C_{20}$ aryl group, a $C_2$-$C_{20}$ heteroaryl group, a $C_6$-$C_{20}$ aryloxy group, or a $C_2$-$C_{20}$ heteroaryloxy group that may be substituted with $Z^2$, and respective $R^3$ to $R^6$ may be identical or different with each other;

$Z^1$ represents a halogen atom, a nitro group, a cyano group, or a $C_6$-$C_{20}$ aryl group, a $C_2$-$C_{20}$ heteroaryl group, a $C_1$-$C_{20}$ alkoxy group, a $C_2$-$C_{20}$ alkenyloxy group, or a $C_2$-$C_{20}$ alkynyloxy group that may be substituted with $Z^3$;

$Z^2$ represents a halogen atom, a nitro group, a cyano group, or a $C_1$-$C_{20}$ alkyl group, a $C_2$-$C_{20}$ alkenyl group, a $C_2$-$C_{20}$ alkynyl group, a $C_1$-$C_{20}$ alkoxy group, a $C_2$-$C_{20}$ alkenyloxy group, a $C_2$-$C_{20}$ alkynyloxy group, a $C_6$-$C_{20}$ aryl group, or a $C_2$-$C_{20}$ heteroaryl group that may be substituted with $Z^3$;

$Z^3$ represents a halogen atom, a nitro group, or a cyano group;

letters $m^1$ and $m^2$ respectively represent the numbers of substituents $R^5$ and $R^6$, and each independently represent an integer of 0 to 4; and letters $n^1$ and $n^2$ respectively represent the numbers of substituents $R^3$ and $R^4$, and each independently represent an integer of 0 to 3.

2. The polymer of 1, wherein the polymer has a weight average molecular weight of 1,000 to 200,000.
3. The polymer of 1 or 2, wherein A is a perfluoromethanediyl group, a perfluoroethane-1,2-diyl group, a perfluoropropane-1,3-diyl group, a perfluoropropane-2,2-diyl group, a perfluorobutane-1,4-diyl group, a perfluoropentane-1,5-diyl group, or a perfluorohexane-1,6-diyl group.
4. The polymer of any one of 1 to 3, wherein both of $R^1$ and $R^2$ are an alkoxy group, an alkenyloxy group, an alkynyloxy group, an aryloxy group, a heteroaryloxy group, or an alkyl group including at least one ether structure.
5. A charge-transporting substance consisting of the polymer of any one of 1 to 4.
6. A charge-transporting varnish containing the charge-transporting substance of 5, a fluorine-atom-free charge-transporting substance, a dopant consisting of a heteropoly-acid, and an organic solvent.
7. The charge-transporting varnish of 6, wherein the fluorine-atom-free charge-transporting substance is an aniline derivative.
8. A charge-transporting thin film is produced by use of the charge-transporting varnish of 6 or 7.
9. An electronic device containing the charge-transporting thin film of 8.
10. An organic electroluminescent element containing the charge-transporting thin film of 8.
11. A method of producing a charge-transporting thin film, containing applying the charge-transporting varnish according of 6 or 7 to a substrate, and evaporating off the solvent.
12. A fluorine-atom-containing triphenylamine derivative is represented by the following formula:

[Chemical Formula 2]

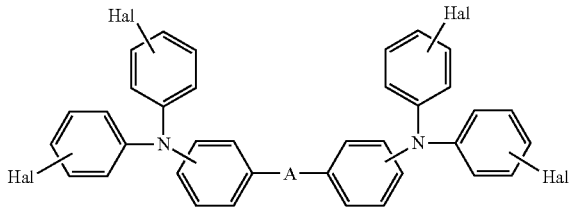

wherein A represents a $C_1$-$C_6$ fluoroalkanediyl group, and Hal each independently represent a halogen atom or a pseudo-halogen group.

Advantageous Effects of the Invention

The fluorine-atom-containing polymers of the present invention can be suitably used as a charge-transporting substance, and, even where charge-transporting varnishes of the present invention containing the fluorine-atom-containing polymer are used to form a thin film as a single layer between and in contact with an anode and a light-emitting layer, it is possible to realize an organic EL element having excellent luminance characteristics. The reason for this has not yet been elucidated, but is surmised as follows. The fluorine-atom-containing charge-transporting substance is liable to migrate toward the front surface side (light-emitting layer side) of the thin film. Therefore, the fluorine-atom-containing charge-transporting substance is predominantly present on the front surface side (light-emitting layer side) of the thin film, whereas the fluorine-atom-free charge-transporting substance is predominantly present on the back surface side (anode side) of the thin film. Thus, phase separation into a hole injection portion and a hole transport portion occurs within the single layer. Accordingly, the hole-injecting component decreases, whereas the hole-transporting component increases, along the direction from the anode toward the light-emitting layer. As a result of this, it is conjectured, the single layer functions as a hole injection and transport layer, like in the case where a hole injection layer and a hole transport layer are present.

Besides, by use of the charge-transporting varnishes of the present invention, a functional multilayer film in an element can be converted to a single film. Accordingly, it is possible, through simplification of production process conditions, to contrive an enhanced yield and a lowered cost, or to make the element lighter in weight and compact. In addition, the charge-transporting varnishes of the present invention enable a thin film excellent in charge-transporting properties to be produced with good reproducibility, even when wet processes capable of forming a film over a large area, such as the spin coating method and the slit coating method, are used. Therefore, the charge-transporting varnishes make it possible to sufficiently cope with the progress in the field of organic EL elements in recent years.

Further, the thin films obtained from the charge-transporting varnishes of the present invention can be used also as anti-static films, anode buffer layers in organic thin film solar cells, and the like.

EMBODIMENT FOR CARRYING OUT THE INVENTION

[Fluorine-Atom-Containing Polymer]

The fluorine-atom-containing polymer of the present invention is a condensation polymer of a fluorine-atom-containing triphenylamine derivative giving a repeating unit represented by formula (1) and a fluorene derivative giving a repeating unit represented by formula (2).

[Chemical Formula 3]

(1)

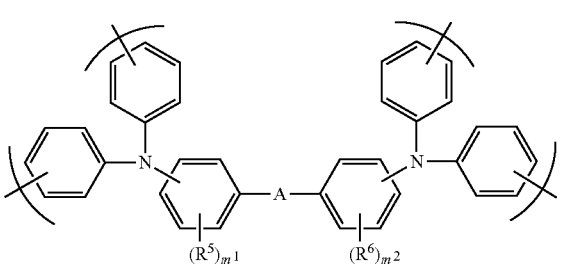

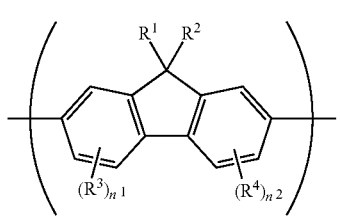
(2)

The repeating unit represented by formula (1), in consideration of the availability of the fluorine-atom-containing triphenylamine derivative as the starting material and solubility of the polymer obtained in organic solvents, is preferably one that is represented by formula (1') or formula (1'').

[Chemical Formula 4]

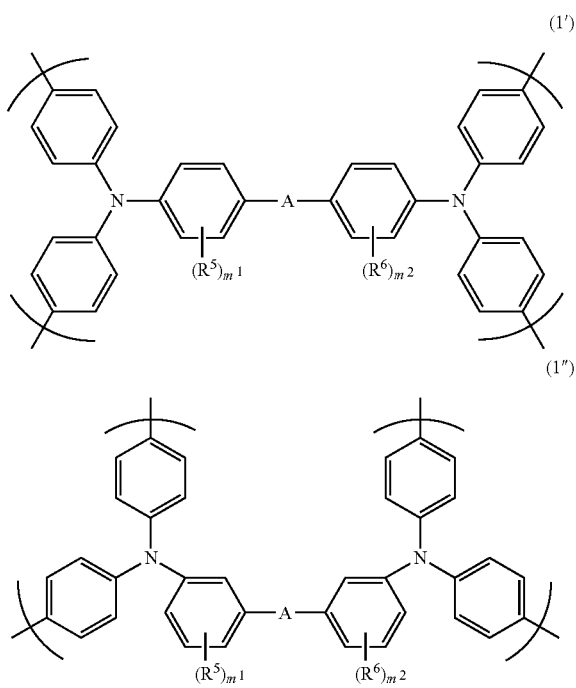

In formulas (1), (1'), and (1''), A represents a $C_1$-$C_6$ fluoroalkanediyl group. The fluoroalkanediyl group is not particularly limited so long as it is a group obtained by substituting part or all of hydrogen atoms bonded to a carbon atom of an alkanediyl group with a fluorine atom.

Specific examples of the fluoroalkanediyl group include monofluoromethanediyl group, perfluoromethanediyl group, 2,2,2-trifluoroethane-1,1-diyl group, perfluoroethane-1,1-diyl group, perfluoroethane-1,2-diyl group, 3-fluoropropane-1,2-diyl group, 3,3,3-trifluoropropane-1,1-diyl group, 1,1-difluoropropane-1,3-diyl group, perfluoropropane-1,1-diyl group, perfluoropropane-1,2-diyl group, perfluoropropane-1,3-diyl group, perfluoropropane-2,2-diyl group, 2-methyl-2-fluoropropane-1,3-diyl group, 3,4,4-trifluorobutane-1,2-diyl group, 4,4,4-trifluorobutane-1,3-diyl group, 2,2,3,3-tetrafluorobutane-1,4-diyl group, perfluorobutane-1,1-diyl group, perfluorobutane-1,2-diyl group, perfluorobutane-1,3-diyl group, perfluorobutane-1,4-diyl group, 1-fluoropentane-1,1-diyl group, 4,5,5-trifluoropentane-1,5-diyl group, 2,2,3,3,4,4-hexafluoropentane-1,5-diyl group, perfluoropenetane-1,1-diyl group, perfluoropentane-1,2-diyl group, perfluoropentane-1,3-diyl group, perfluoropentane-1, 4-diyl group, perfluoropentane-1,5-diyl group, 2,2,3,3,4,4, 5,5-octafluorohexane-1,6-diyl group, perfluorohexane-1,1-diyl group, perfluorohexane-1,2-diyl group, perfluorohexane-1,3-diyl group, perfluorohexane-1,4-diyl group, perfluorohexane-1,5-diyl group, and perfluorohexane-1,6-diyl group.

The fluoroalkanediyl group is preferably a perfluoroalkanediyl group (namely, a group obtained by substituting all of hydrogen atoms bonded to a carbon atom of an alkanediyl group with a fluorine atom) of 1 to 6 carbon atoms, and particularly preferable examples thereof include perfluoromethanediyl group, perfluoroethane-1,2-diyl group, perfluoropropane-1,3-diyl group, perfluoropropane-2,2-diyl group, perfluorobutane-1,4-diyl group, perfluoropentane-1, 5-diyl group, and perfluorohexane-1,6-diyl group.

In formula (2), $R^1$ and $R^2$ each independently represent a hydrogen atom, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_2$-$C_{20}$ heteroaryl group, a $C_1$-$C_{20}$ alkoxy group, a $C_2$-$C_{20}$ alkenyloxy group, a $C_2$-$C_{20}$ alkynyloxy group, a $C_6$-$C_{20}$ aryloxy group, a $C_2$-$C_{20}$ heteroaryloxy group, or a $C_2$-$C_{20}$ alkyl group including at least one ether structure. At least one of $R^1$ and $R^2$ represents any of the alkoxy group, the alkenyloxy group, the alkynyloxy group, the aryloxy group, the heteroaryloxy group, and the alkyl group including at least one ether structure.

In formulas (1) and (2), $R^3$ to $R^6$ each independently represent a halogen atom, a nitro group, a cyano group, a $C_1$-$C_{20}$ alkyl group, a $C_2$-$C_{20}$ alkenyl group, a $C_2$-$C_{20}$ alkynyl group, a $C_1$-$C_{20}$ alkoxy group, a $C_2$-$C_{20}$ alkenyloxy group, or a $C_2$-$C_{20}$ alkynyloxy group that may be substituted with $Z^1$, or a $C_6$-$C_{20}$ aryl group, a $C_2$-$C_{20}$ heteroaryl group, a $C_6$-$C_{20}$ aryloxy group, or a $C_2$-$C_{20}$ heteroaryloxy group that may be substituted with $Z^2$. Here, respective $R^3$ to $R^6$ may be identical or different with each other.

$Z^1$ represents a halogen atom, a nitro group, a cyano group, or a $C_6$-$C_{20}$ aryl group, a $C_2$-$C_{20}$ heteroaryl group, a $C_1$-$C_{20}$ alkoxy group, a $C_2$-$C_{20}$ alkenyloxy group, or a $C_2$-$C_{20}$ alkynyloxy group that may be substituted with Z3.

$Z^2$ represents a halogen atom, a nitro group, a cyano group, or a $C_1$-$C_{20}$ alkyl group, a $C_2$-$C_{20}$ alkenyl group, a $C_2$-$C_{20}$ alkynyl group, a $C_1$-$C_{20}$ alkoxy group, a $C_2$-$C_{20}$ alkenyloxy group, a $C_2$-$C_{20}$ alkynyloxy group, a $C_6$-$C_{20}$ aryl group, or a $C_2$-$C_{20}$ heteroaryl group that may be substituted with $Z^3$.

$Z^3$ represents a halogen atom, a nitro group, or a cyano group.

Examples of the halogen atom include a fluorine atom, a chlorine atom, a bromine atom, and an iodine atom.

The $C_1$-$C_{20}$ alkyl group may be any of straight-chain, branched, and cyclic groups, and specific examples thereof include: $C_1$-$C_{20}$ straight-chain or branched alkyl groups such as methyl, ethyl, n-propyl, isopropyl, n-butyl, isobutyl, s-butyl, t-butyl, n-pentyl, n-hexyl, n-heptyl, n-octyl, n-nonyl, and n-decyl; and $C_3$-$C_{20}$ cycloalkyl groups such as cyclopropyl, cyclobutyl, cyclopentyl, cyclohexyl, cycloheptyl, cyclooctyl, cyclononyl, cyclodecyl, bicyclobutyl, bicyclopentyl, bicyclohexyl, bicycloheptyl, bicyclooctyl, bicyclononyl, and bicyclodecyl.

The $C_2$-$C_{20}$ alkenyl group may be any of straight-chain, branched, and cyclic groups, and specific examples thereof include ethenyl, n-1-propenyl, n-2-propenyl, 1-methylethenyl, n-1-butenyl, n-2-butenyl, n-3-butenyl, 2-methyl-1-propenyl, 2-methyl-2-propenyl, 1-ethylethenyl, 1-methyl-1-propneyl, 1-methyl-2-propenyl, n-1-pentenyl, n-1-decenyl, and n-1-eicosenyl.

The $C_2$-$C_{20}$ alkynyl group may be any of straight-chain, branched, and cyclic groups, and specific examples thereof include ethynyl, n-1-propynyl, n-2-propynyl, n-1-butynyl, n-2-butynyl, n-3-butynyl, 1-methyl-2-propynyl, n-1-pentynyl, n-2-pentynyl, n-3-pentynyl, n-4-pentynyl, 1-methyl-n-butynyl, 2-methyl-n-butynyl, 3-methyl-n-butynyl, 1,1-dimethyl-n-propynyl, n-1-hexynyl, n-1-decynyl, n-1-pentadecynyl, and n-1-eicosynyl.

Specific examples of the $C_6$-$C_{20}$ aryl group include phenyl, 1-naphthyl, 2-naphthyl, 1-anthryl, 2-anthryl, 9-anthryl, 1-phenanthryl, 2-phenanthryl, 3-phenanthryl, 4-phenanthryl, and 9-phenanthryl.

Specific examples of the $C_2$-$C_{20}$ heteroaryl group include 2-thienyl, 3-thienyl, 2-furanyl, 3-furanyl, 2-oxazolyl, 4-oxazolyl, 5-oxazolyl, 3-isooxazolyl, 4-isooxazolyl, 5-isooxazolyl, 2-thiazolyl, 4-thiazolyl, 5-thiazolyl, 3-isothiazolyl, 4-isothiazolyl, 5-isothiazolyl, 2-imidazolyl, 4-imidazolyl, 2-pyridyl, 3-pyridyl, and 4-pyridyl.

The $C_1$-$C_{20}$ alkoxy group may be any of straight-chain, branched, and cyclic groups, and specific examples thereof include: $C_1$-$C_{20}$ straight-chain or branched alkoxy groups such as methoxy, ethoxy, n-propoxy, isopropoxy, n-butoxy, isobutoxy, s-butoxy, t-butoxy, n-pentyloxy, n-hexyloxy, n-heptyloxy, n-octyloxy, n-nonyloxy, and n-decyloxy; and $C_3$-$C_{20}$ cycloalkoxy groups such as cyclopropyloxy, cyclobutyloxy, cyclopentyloxy, cyclohexyloxy, cycloheptyloxy, cyclooctyloxy, cyclononyloxy, cyclodecyloxy, bicyclobutyloxy, bicyclopentyloxy, bicyclohexyloxy, bicycloheptyloxy, bicyclooctyloxy, bicyclononyloxy, and bicyclodecyloxy.

The $C_2$-$C_{20}$ alkenyloxy group may be any of straight-chain, branched, and cyclic groups, and specific examples thereof include ethenyloxy, n-1-propenyloxy, n-2-propenyloxy, 1-methylethenyloxy, n-1-butenyloxy, n-2-butenyloxy, n-3-butenyloxy, 2-methyl-1-propenyloxy, 2-methyl-2-propenyloxy, 1-ethylethenyloxy, 1-methyl-1-propnenyloxy, 1-methyl-2-propenyloxy, n-1-penteneyloxy, n-1-decenyloxy, and n-1-eicosenyloxy.

The $C_2$-$C_{20}$ alkynyloxy group may be any of straight-chain, branched, and cyclic groups, and specific examples thereof include ethynyloxy, n-1-propynyloxy, n-2-propynyloxy, n-1-butynyloxy, n-2-butynyloxy, n-3-butynyloxy, 1-methyl-2-propynyloxy, n-1-pentynyloxy, n-2-pentynyloxy, n-3-pentynyloxy, n-4-pentynyloxy, 1-methyl-n-butynyloxy, 2-methyl-n-butynyloxy, 3-methyl-n-butynyloxy, 1,1-dimethyl-n-propynyloxy, n-1-hexynyloxy, n-1-decynyloxy, n-1-pentadecynyloxy, and n-1-eicosynyloxy.

Specific examples of the $C_6$-$C_{20}$ aryloxy group include phenyloxy, 1-naphthyloxy, 2-naphthyloxy, 1-anthryloxy, 2-anthryloxy, 9-anthryloxy, 1-phenanthryloxy, 2-phenanthryloxy, 3-phenanthryloxy, 4-phenanthryloxy, and 9-phenanthryloxy.

Specific examples of the $C_2$-$C_{20}$ heteroaryloxy group include 2-thienyloxy, 3-thienyloxy, 2-furanyloxy, 3-furanyloxy, 2-oxazolyloxy, 4-oxazolyloxy, 5-oxazolyloxy, 3-isooxazolyloxy, 4-isooxazolyloxy, 5-isooxazolyloxy, 2-thiazolyloxy, 4-thiazolyloxy, 5-thiazolyloxy, 3-isothiazolyloxy, 4-isothiazolyloxy, 5-isothiazolyloxy, 2-imidazolyloxy, 4-imidazolyloxy, 2-pyridyloxy, 3-pyridyloxy, and 4-pyridyloxy.

Examples of the $C_2$-$C_{20}$ alkyl group including at least one ether structure include straight-chain or branched alkyl groups in which al least one methylene group has been substituted with an oxygen atom. Such a group, in consideration of availability of a starting compound therefor, is preferably a group represented by formula (A), more preferably a group represented by formula (B).

$$-(RO)_r-R' \tag{A}$$

$$-(CH_2CH_2O)_r-CH_3 \tag{B}$$

Herein R represents a $C_1$-$C_4$ straight-chain or branched alkylene group, R' represents a straight-chain or branched alkyl group of 1 to [20−(the number of carbon atoms in R)×r] carbon atoms, and letter r represents an integer of 1 to 9. From the viewpoint of compatibility with a dopant, r is preferably at least 2, more preferably at least 3, and, from the viewpoint of availability of a starting compound, r is preferably up to 5, more preferably up to 4.

Examples of the $C_2$-$C_{20}$ alkyl group including at least one ether structure include —$CH_2OCH_3$, —$CH_2OCH_2CH_3$, —$CH_2O(CH_2)_2CH_3$, —$CH_2OCH(CH_3)_2$, —$CH_2O(CH_2)_3CH_3$, —$CH_2OCH_2CH(CH_3)_2$, —$CH_2OC(CH_3)_3$, —$CH_2O(CH_2)_4CH_3$, —$CH_2OCH(CH_3)(CH_2)_2CH_3$, —$CH_2O(CH_2)_2CH(CH_3)_2$, —$CH_2OCH(CH_3)(CH_2)_3CH_3$, —$CH_2O(CH_2)_5CH_3$, —$CH_2OCH_2CH(CH_3)(CH_2)_2CH_3$, —$CH_2O(CH_2)_2CH(CH_3)CH_2CH_3$, —$CH_2O(CH_2)_3CH(CH_3)_2$, —$CH_2OC(CH_3)_2(CH_2)_2CH_3$, —$CH_2OCH(CH_2CH_3)(CH_2)_2CH_3$, —$CH_2OC(CH_3)_2CH(CH_3)_2$, —$CH_2O(CH_2)_6CH_3$, —$CH_2O(CH_2)_7CH_3$, —$CH_2OCH_2CH(CH_2CH_3)(CH_2)_3CH_3$, —$CH_2O(CH_2)_8CH_3$, —$CH_2O(CH_2)_9CH_3$, —$CH_2O(CH_2)_{10}CH_3$, —$CH_2O(CH_2)_{11}CH_3$, —$CH_2O(CH_2)_{12}CH_3$, —$CH_2O(CH_2)_{13}CH_3$, —$CH_2O(CH_2)_{14}CH_3$, —$CH_2O(CH_2)_{15}CH_3$, —$CH_2O(CH_2)_{16}CH_3$, —$CH_2O(CH_2)_{17}CH_3$, —$CH_2O(CH_2)_{18}CH_3$, —$CH_2CH_2OCH_3$, —$CH_2OCH_2CH_3$, —$CH_2CH_2O(CH_2)_2CH_3$, —$CH_2CH_2OCH(CH_3)_2$, —$CH_2CH_2O(CH_2)_3CH_3$, —$CH_2CH_2OCH_2CH(CH_3)_2$, —$CH_2OC(CH_3)_3$, —$CH_2CH_2O(CH_2)_4CH_3$, —$CH_2CH_2OCH(CH_3)(CH_2)_2CH_3$, —$CH_2CH_2O(CH_2)_2CH(CH_3)_2$, —$CH_2CH_2OCH(CH_3)(CH_2)_3CH_3$, —$CH_2CH_2O(CH_2)_5CH_3$, —$CH_2CH_2OCH_2CH(CH_3)(CH_2)_2CH_3$, —$CH_2CH_2O(CH_2)_2CH(CH_3)CH_2CH_3$, —$CH_2CH_2O(CH_2)_3CH(CH_3)_2$, —$CH_2CH_2OC(CH_3)_2(CH_2)_2CH_3$, —$CH_2CH_2OCH(CH_2CH_3)(CH_2)_2CH_3$, —$CH_2CH_2OC(CH_3)_2CH(CH_3)_2$, —$CH_2CH_2O(CH_2)_6CH_3$, —$CH_2CH_2O(CH_2)_7CH_3$, —$CH_2CH_2OCH_2CH(CH_2CH_3)(CH_2)_3CH_3$, —$CH_2CH_2O(CH_2)_8CH_3$, —$CH_2CH_2O(CH_2)_9CH_3$, —$CH_2CH_2O(CH_2)_{10}CH_3$, —$CH_2CH_2O(CH_2)_{11}CH_3$, —$CH_2CH_2O(CH_2)_{12}CH_3$, —$CH_2CH_2O(CH_2)_{13}CH_3$, —$CH_2CH_2O(CH_2)_{14}CH_3$, —$CH_2CH_2O(CH_2)_{15}CH_3$, —$CH_2CH_2O(CH_2)_{16}CH_3$, —$CH_2CH_2O(CH_2)_{17}CH_3$, —$CH_2CH_2CH_2OCH_3$, —$CH_2CH_2CH_2OCH_2CH_3$, —$CH_2CH_2CH_2O(CH_2)_2CH_3$, —$CH_2CH_2CH_2OCH(CH_3)_2$, —$CH_2CH_2CH_2O(CH_2)_3CH_3$, —$CH_2CH_2CH_2OCH_2CH(CH_3)_2$, —$CH_2CH_2CH_2OC(CH_3)_3$, —$CH_2CH_2CH_2O(CH_2)_4CH_3$, —$CH_2CH_2CH_2OCH(CH_3)(CH_2)_2CH_3$, —$CH_2CH_2CH_2O(CH_2)_2CH(CH_3)_2$, —$CH_2CH_2CH_2OCH(CH_3)(CH_2)_3CH_3$, —$CH_2CH_2O(CH_2)_5CH_3$, —$CH_2CH_2CH_2OCH_2CH(CH_3)(CH_2)_2CH_3$, —$CH_2CH_2CH_2O(CH_2)_2CH(CH_3)CH_2CH_3$, —$CH_2CH_2CH_2O(CH_2)_3CH(CH_3)_2$, —$CH_2CH_2CH_2OC(CH_3)_2(CH_2)_2CH_3$, —$CH_2CH_2CH_2OCH(CH_2CH_3)(CH_2)_2CH_3$, —$CH_2CH_2CH_2OC(CH_3)_2CH(CH_3)_2$, —$CH_2CH_2O(CH_2)_6CH_3$, —$CH_2CH_2O(CH_2)_7CH_3$, —$CH_2CH_2CH_2OCH_2CH(CH_2CH_3)(CH_2)_3CH_3$, —$CH_2CH_2OCH_2CH_2OCH_3$, —$CH_2CH_2OCH_2CH_2OCH_2CH_2OCH_3$, —$CH_2CH_2OCH_2CH_2OCH_2CH_2OCH_2OCH_3$, —$CH_2CH_2OCH_2CH_2OCH_2CH_2OCH_2CH_2OCH_2CH_2OCH_3$, —CH$_2$CH$_2$OCH$_2$CH$_2$OCH$_2$CH$_2$OCH$_2$CH$_2$OCH$_2$CH$_2$OCH$_2$CH$_2$OCH$_3$,
—CH$_2$CH$_2$OCH$_2$CH$_2$OCH$_2$CH$_2$OCH$_2$CH$_2$OCH$_2$CH$_2$OCH$_2$CH$_2$OCH$_2$CH$_2$OCH$_3$,
—CH$_2$CH$_2$OCH$_2$CH$_2$OCH$_2$CH$_2$OCH$_2$CH$_2$OCH$_2$CH$_2$OCH$_2$CH$_2$OCH$_2$CH$_2$OCH$_3$,
—CH$_2$CH$_2$CH$_2$OCH$_2$CH$_2$CH$_2$OCH$_3$,
—CH$_2$CH$_2$CH$_2$OCH$_2$CH$_2$CH$_2$OCH$_2$CH$_2$CH$_2$OCH$_3$,
—CH$_2$CH$_2$CH$_2$OCH$_2$CH$_2$CH$_2$OCH$_2$CH$_2$CH$_2$OCH$_2$CH$_2$CH$_2$OCH$_3$,
—CH$_2$CH$_2$CH$_2$OCH$_2$CH$_2$CH$_2$OCH$_2$CH$_2$CH$_2$OCH$_2$CH$_2$CH$_2$OCH$_3$,
—CH$_2$CH$_2$CH$_2$OCH$_2$CH$_2$CH$_2$OCH$_2$CH$_2$CH$_2$OCH$_2$CH$_2$CH$_2$OCH$_2$CH$_2$CH$_2$OCH$_3$,
—CH$_2$CH$_2$CH$_2$CH$_2$OCH$_2$CH$_2$CH$_2$CH$_2$OCH$_2$CH$_2$CH$_2$CH$_2$OCH$_3$,
—CH$_2$CH$_2$CH$_2$CH$_2$OCH$_2$CH$_2$CH$_2$CH$_2$OCH$_2$CH$_2$CH$_2$CH$_2$OCH$_2$CH$_2$CH$_2$CH$_2$OCH$_3$,
—CH$_2$CH$_2$OCH$_2$CH$_2$OCH$_2$CH$_2$OCH$_2$CH$_2$OCH$_2$CH$_2$OCH$_2$CH$_2$OCH$_2$CH$_3$,
—CH$_2$CH$_2$OCH$_2$CH$_2$OCH$_2$CH$_2$OCH$_2$CH$_2$OCH$_2$CH$_2$OCH$_2$CH$_2$OCH$_2$CH$_3$,
—CH$_2$CH$_2$OCH$_2$CH$_2$OCH$_2$CH$_2$OCH$_2$CH$_2$OCH$_2$CH$_2$OCH$_2$CH$_2$OCH$_2$CH$_2$OCH$_2$CH$_3$,
—CH$_2$CH$_2$OCH$_2$CH$_2$OCH$_2$CH$_3$,
—CH$_2$CH$_2$OCH$_2$CH$_2$OCH$_2$CH$_2$OCH$_2$CH$_3$,
—CH$_2$CH$_2$CH$_2$O(CH$_2$)$_8$CH$_3$, —CH$_2$CH$_2$CH$_2$O(CH$_2$)$_9$CH$_3$, —CH$_2$CH$_2$CH$_2$O(CH$_2$)$_{10}$CH$_3$, —CH$_2$CH$_2$CH$_2$O(CH$_2$)$_{11}$CH$_3$, —CH$_2$CH$_2$CH$_2$O(CH$_2$)$_{12}$CH$_3$, —CH$_2$CH$_2$CH$_2$O(CH$_2$)$_{13}$CH$_3$, —CH$_2$CH$_2$CH$_2$O(CH$_2$)$_{14}$CH$_3$, —CH$_2$CH$_2$CH$_2$O(CH$_2$)$_{15}$CH$_3$, and —CH$_2$CH$_2$CH$_2$O(CH$_2$)$_{16}$CH$_3$.

In the present invention, in order that both good solubility of the fluorine-atom-containing polymer obtained in organic solvents and good compatibility of the polymer with a dopant in the case of forming the polymer into a solid film (charge-transporting thin film) are realized, at least one of $R^1$ and $R^2$ is the alkoxy group, the alkenyloxy group, the alkynyloxy group, the aryloxy group, the heteroaryloxy group, or the alkyl group including at least one ether structure, and, more preferably, both of $R^1$ and $R^2$ are any of these groups. Besides, in consideration of availability of the starting compound, charge-transporting properties of the polymer obtained and the thin film obtained, it is preferable that one of $R^1$ and $R^2$ is a group represented by formula (A), and, more preferably, both of $R^1$ and $R^2$ are a group represented by formula (A).

In formula (1), $m^1$ and $m^2$ represent the numbers of the substituents $R^5$ and $R^6$, respectively, and they each independently represent an integer of 0 to 4. From the viewpoints of availability of the starting compound, solubility of the polymer of the present invention, enhancement of charge-transporting properties and the like, the integer is preferably 0 to 2, more preferably 0 or 1. It is particularly preferable that both of $m^1$ and $m^2$ are 0 or 1.

In formula (2), $n^1$ and $n^2$ represent the numbers of the substituents $R^3$ and $R^4$, respectively, and they each independently represent an integer of 0 to 3. From the viewpoints of availability of the starting compound, solubility of the polymer of the present invention, enhancement of charge-transporting properties and the like, the integer is preferably 0 to 2, more preferably 0 or 1, and most preferably 0. It is particularly preferable that both of $n^1$ and $n^2$ are 0.

The lower limit for the weight average molecular weight of the fluorine-atom-containing polymer of the present invention is preferably 1,000, more preferably 5,000, and further preferably 10,000, from the viewpoint of enhancing charge-transporting properties. The upper limit for the weight average molecular weight is preferably 200,000, more preferably 150,000, and further preferably 100,000, from the viewpoint of enhancing the solubility of the polymer. Note that the weight average molecular weight in the present invention is a polystyrene-basis weight average molecular weight obtained by gel permeation chromatography (GPC).

[Method of Synthesizing Fluorine-Atom-Containing Polymer]

The fluorine-atom-containing polymer of the present invention can be synthesized by condensation polymerization of a fluorine-atom-containing triphenylamine derivative giving a repeating unit represented by formula (1) with a fluorene derivative giving a repeating unit represented by formula (2).

One example of the synthesizing method is condensation polymerization of a triphenylamine derivative represented by formula (3) with a fluorene derivative represented by formula (4-1) or formula (4-2), as represented by the following scheme A.

[Chemical Formula 5]

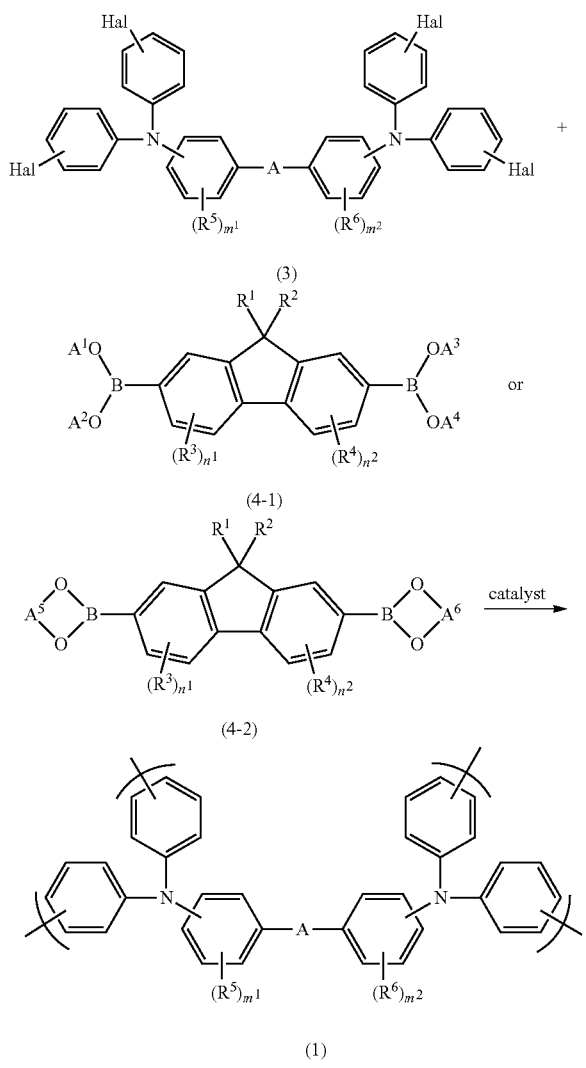

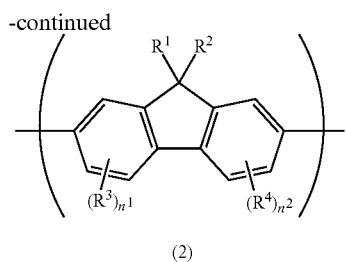

Herein, A, $R^1$ to $R^6$, $m^1$, $m^2$, $n^1$, and $n^2$ are as defined above. Hal each independently represent a halogen atom or a pseudo-halogen group. $A^1$ to $A^4$ each independently represent a hydrogen atom, a $C_1$-$C_{20}$ alkyl group, or a $C_6$-$C_{20}$ aryl group. $A^5$ and $A^6$ each independently represent a $C_1$-$C_{20}$ alkanediyl group or a $C_6$-$C_{20}$ arylene group.

A fluorine-atom-containing polymer wherein the repeating unit represented by formula (1) is one represented by formula (1') or (1") can be synthesized by using a triphenylamine derivative represented by formula (3') or formula (3") as the triphenylamine derivative represented by formula (3).

[Chemical Formula 6]

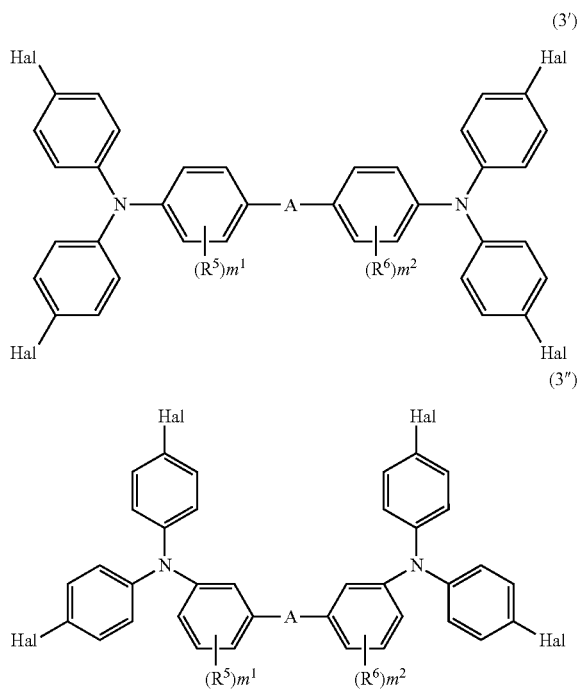

Herein, $R^5$, $R^6$, $m^1$, $m^2$, A and Hal are as defined above.

Examples of the pseudo-halogen group include methanesulfonyloxy group, fluoroalkylsulfonyloxy groups such as trifluoromethanesulfonyloxy or nonafluorobutanesulfonyloxy, and aromatic sulfonyloxy groups such as benzenesulfonyloxy or toluenesulfonyloxy.

Specific examples of the halogen atom and the alkyl and aryl groups of $A^1$ to $A^4$ include the same ones as above-mentioned.

Examples of the $C_1$-$C_{20}$ alkanediyl group include ethylene, propane-1,2-diyl, propane-1,3-diyl, 2,2-dimethylpropane-1,3-diyl, 2-ethyl-2-methylpropane-1,3-diyl, 2,2-diethylpropane-1,3-diyl, 2-methyl-2-propylpropane-1,3-diyl, butane-1,3-diyl, butane-2,3-diyl, butane-1,4-diyl, 2-methylbutane-2,3-diyl, 2,3-dimethylbutane-2,3-diyl, pentane-1,3-diyl, pentane-1,5-diyl, pentane-2,3-diyl, pentane-2,4-diyl, 2-methylpentane-2,3-diyl, 3-methylpentane-2,3-diyl, 4-methylpentane-2,3-diyl, 2,3-dimethylpentane-2,3-diyl, 3-methylpentane-2,4-diyl, 3-ethylpentane-2,4-diyl, 3,3-dimethylpentane-2,4-diyl, 3,3-dimethylpentane-2,4-diyl, 2,4-dimethylpentane-2,4-diyl, hexane-1,6-diyl, hexane-1,2-diyl, hexane-1,3-diyl, hexane-2,3-diyl, hexane-2,4-diyl, hexane-2,5-diyl, 2-methylhexane-2,3-diyl, 4-methylhexane-2,3-diyl, 3-methylhexane-2,4-diyl, 2,3-dimethylhexane-2,4-diyl, 2,4-dimethylhexane-2,4-diyl, 2,5-dimethylhexane-2,4-diyl, 2-methylhexane-2,5-diyl, 3-methylhexane-2,5-diyl, and 2,5-dimethylhexane-2,5-diyl.

Examples of the $C_6$-$C_{20}$ arylene group include 1,2-phenylene, 1,2-naphthylene, 2,3-naphthylene, 1,8-naphthylene, 1,2-anthrylene, 2,3-anthrylene, 1,2-phenanthrylene, 3,4-phenanthrylene, and 9,10-phenanthrylene.

Examples of a catalyst to be used in the above-mentioned reaction include [1,1'-bis(diphenylphosphino)ferrocene]palladium(II) dichloride ($PdCl_2(dppf)$), tetrakis(triphenylphosphine)palladium ($Pd(PPh_3)_4$), bis(triphenylphosphine)dichloropalladium ($Pd(PPh_3)_2Cl_2$), bis(benzylideneacetone)palladium ($Pd(dba)_2$), tris(benzylideneacetone)dipalladium ($Pd_2(dba)_3$), bis(tri-t-butylphosphine)palladium ($Pd(P-t-Bu_3)_2$), and palladium(II) acetate ($Pd(OAc)_2$).

The ratio of the amount of the triphenylamine derivative represented by formula (3) to be used to the amount of the fluorene derivative represented by formula (4-1) or (4-2) to be used, in molar ratio, is preferably in the range from approximately 1:1 to 1:3.

The triphenylamine derivative represented by formula (3) can be synthesized as follows. As represented by the following scheme B, an amine compound represented by formula (6) and a halogenated compound represented by formula (7) are reacted with each other in the presence of a catalyst, to synthesize a triphenylamine derivative represented by formula (5). Alternatively, as represented by the following scheme C, a halogenated compound represented by formula (8) and a diphenylamine are reacted with each other in the presence of a catalyst, to synthesize a triphenylamine derivative represented by formula (5). Then, as represented by the following scheme D, the triphenylamine derivative represented by formula (5) is reacted with a known halogenating agent, to obtain the triphenylamine derivative represented by formula (3).

[Chemical Formula 7]

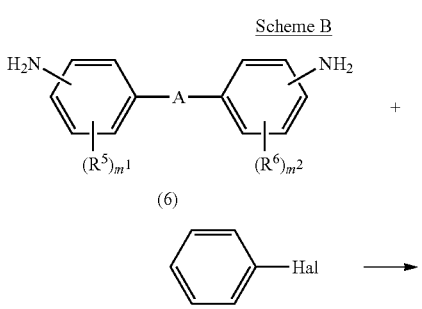

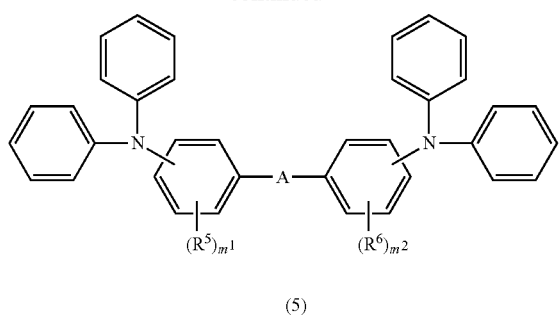

(5)

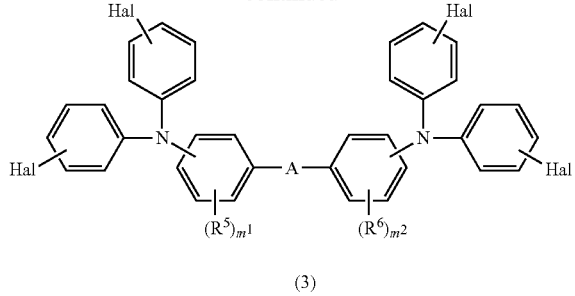

(3)

Herein, $R^5$, $R^6$, $m^1$, $m^2$, A, and Hal are as defined above.

In addition, the triphenylamine derivative represented by formula (3') can be synthesized as follows. Using an amine compound represented by formula (6') as the amine compound represented by formula (6), or using a halogenated compound represented by formula (8') as the halogenated compound represented by formula (8), a triphenylamine derivative represented by formula (5') is synthesized according to the above-mentioned scheme B or C. Thereafter, the triphenylamine derivative represented by formula (5') is reacted with a halogenating agent according to the above-mentioned scheme D, to obtain the triphenylamine derivative represented by formula (3').

Scheme C

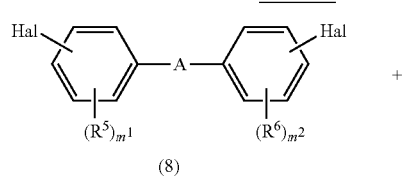

(8)

[Chemical Formula 8]

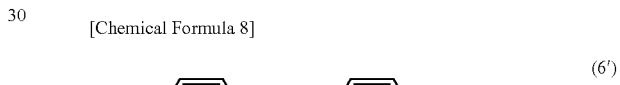

(6')

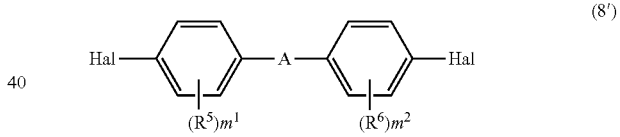

(8')

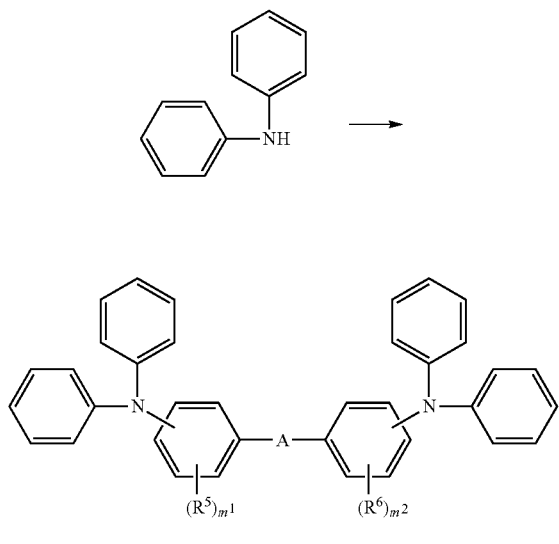

(5)

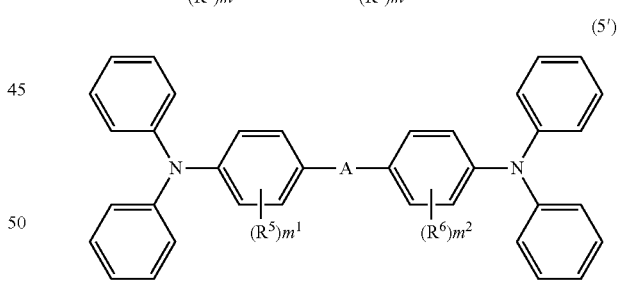

(5')

Herein, $R^5$, $R^6$, $m^1$, $m^2$, A, and Hal are as defined above.

Similarly, the triphenylamine derivative represented by formula (3") can be synthesized as follows. Using an amine compound represented by formula (6") as the amine compound represented by formula (6), or using a halogenated compound represented by formula (8") as the halogenated compound represented by formula (8), a triphenylamine derivative represented by formula (5") is synthesized according to the above-mentioned scheme B or C. Then, the triphenylamine derivative represented by formula (5") is reacted with a halogenating agent according to the above-mentioned scheme D, to obtain the triphenylamine derivative represented by formula (3").

Scheme D

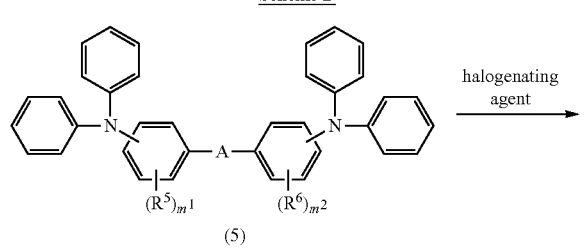

(5)

halogenating agent →

[Chemical Formula 9]

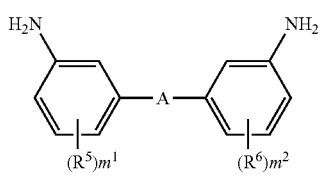
(6″)

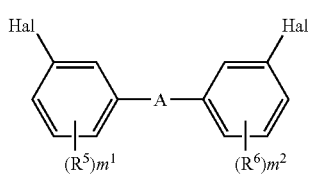
(8″)

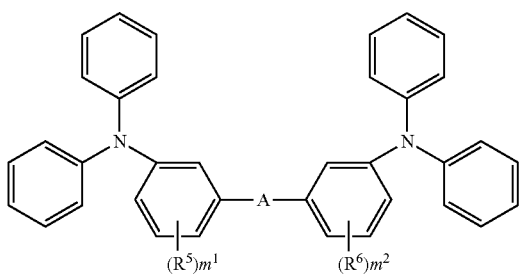
(5″)

Herein, $R^5$, $R^6$, $m^1$, $m^2$, A, and Hal are as defined above.

The ratio between the amount of the amine compound to be used and the amount of the halogenated compound to be used may be such that the whole amount of the Hal groups in the entire halogenated compound is at least one equivalent, preferably approximately 1 to 1.2 equivalents, based on the whole material amount of the NH groups in the entire amine compound.

Examples of the catalyst include: copper catalysts such as copper chloride, copper bromide, and copper iodide; and palladium catalysts such as $Pd(PPh_3)_4$, $Pd(PPh_3)_2Cl_2$, $Pd(dba)_2$, $Pd_2(dba)_3$, $Pd(P\text{-}t\text{-}Bu_3)_2$, and $Pd(OAc)_2$. These catalysts may be used either singly or in combination of at least two of them. Besides, these catalysts may be used together with a known appropriate ligand.

The amount of the catalyst to be used may be 0.0001 to 0.5 mol, preferably approximately 0.001 to 0.1 mol, per 1 mol of the halogenated compound. Where a ligand is used, the amount of the ligand to be used may be 0.5 to 50 equivalents, preferably 1 to 10 equivalents, based on the metal complex used.

As the halogenating agent, known ones can be used, and specific examples thereof include N-bromosuccinimide.

The amount of the halogenating agent to be used is preferably approximately 4 to 6 mol, per 1 mol of the compound represented by formula (5).

Each of the above-mentioned reactions may be carried out in a solvent. Where a solvent is used, the kind of the solvent is not particularly limited, so long as the solvent does not exert any adverse influence on the reaction. Specific examples of the solvent which can be suitably used in the reactions represented by the schemes A and B include aliphatic hydrocarbons (pentane, n-hexane, n-octane, n-decane, and decalin), halogenated aliphatic hydrocarbons (chloroform, dichloromethane, dichloroethane, and carbon tetrachloride), aromatic hydrocarbons (benzene, nitrobenzene, toluene, o-xylene, m-xylene, p-xylene, and mesitylene), ethers (diethyl ether, isopropyl ether, t-butyl methyl ether, tetrahydrofuran (THF), dioxane, 1,2-dimethoxyethane, and 1,2-diethoxyethane), amides (N,N-dimethylformamide (DMF) and N,N-dimethylacetamide), lactams and lactones (N-methylpyrrolidone and γ-butyrolactone), urea derivatives (N,N-dimethylimidazolidinone and tetramethylurea), sulfoxides (dimethyl sulfoxide and sulfolane), nitriles (acetonitrile, propionitrile, and butyronitrile). Besides, specific examples of the solvent which can be suitably used in the reaction represented by the scheme C include halogenated aromatic hydrocarbons (chlorobenzene, bromobenzene, o-dichlorobenzene, m-dichlorobenzene, and p-dichlorobenzene), in addition to the solvents mentioned as examples of the solvent usable in the reactions represented by the schemes A and B. The solvents may be used either singly or in combination of at least two of them.

The reaction temperature may be appropriately set within the range from the melting point to the boiling point of the solvent used. Particularly, the reaction temperature is preferably approximately 0 to 200° C., more preferably 20 to 150° C.

After the reaction is over, a post-treatment is performed according to an ordinary method, whereby the desired triphenylamine derivative can be obtained.

The fluorene derivative represented by formula (4-1) or (4-2) can be synthesized as follows. A compound represented by formula (9) and compounds represented by formulas (10-1) and (10-2) are reacted with one another according to the following scheme E, to synthesize an intermediate represented by formula (11). Thereafter, the intermediate represented by formula (11) is reacted with a boronic acid or a boronic acid ester represented by formula (12-1) or (12-2) in the presence of a catalyst, as represented by the following scheme F1 or F2, to obtain the fluorene derivative represented by formula (4-1) or (4-2).

[Chemical Formula 10]

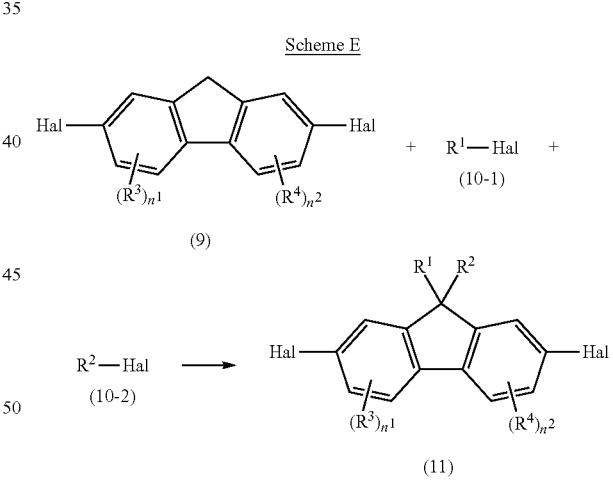

Scheme F1

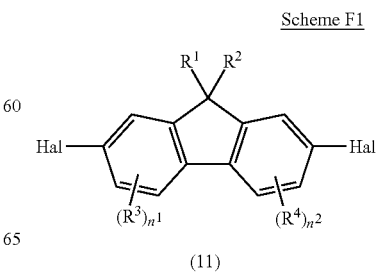

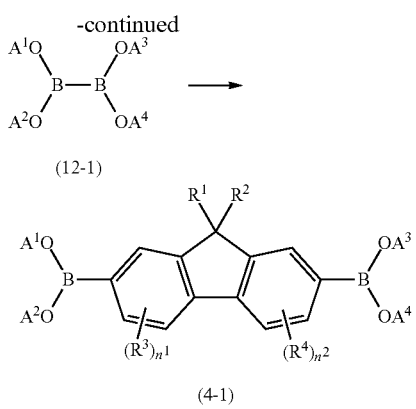

(12-1)

(4-1)

Scheme F2

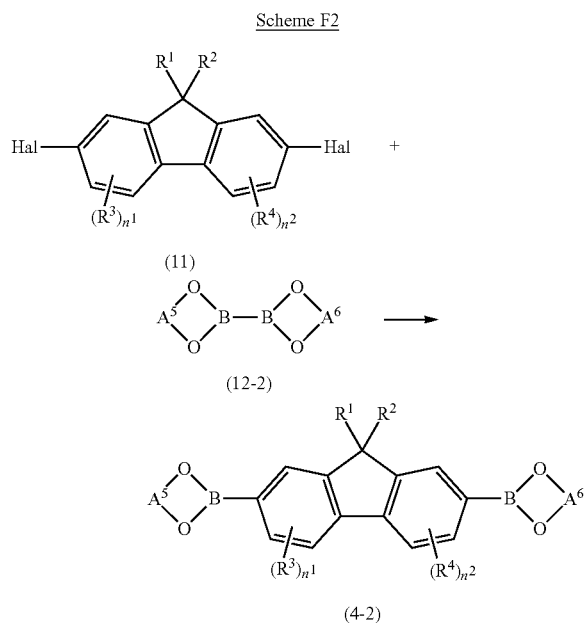

(11)

(12-2)

(4-2)

Herein, Hal, $R^1$ to $R^4$, $A^1$ to $A^6$, $n^1$, and $n^2$ are as defined above.

In the reaction represented by the scheme E, the ratio between the amount of the compound represented by formula (9) to be used and the amount of the compounds represented by formulas (10-1) and (10-2) to be used, in molar ratio, is such that the amount of the compounds represented by formulas (10-1) and (10-2) is approximately 1 to 3 mol, per 1 mol of the compound represented by formula (9).

Examples of the solvent for use in the above reaction include dimethyl sulfoxide, N,N-dimethylformamide, N,N-dimethylacetamide, tetrahydrofuran, dioxane, acetonitrile, and toluene. Among these solvents, preferred is dimethyl sulfoxide, from the viewpoint of good solubility of the starting compounds in the solvent and smooth progress of the reaction.

The reaction temperature may normally be within the range from −50° C. to the boiling point of the solvent, and is preferably in the range of 0 to 100° C. The reaction time is normally 0.1 to 100 hours.

In the reaction represented by the scheme F1 or F2, the ratio between the amount of the compound represented by formula (11) to be used and the amount of the compound represented by formula (12-1) or (12-2) to be used, in molar ratio, is such that the amount of the compound represented by formula (12-1) or (12-2) is approximately 1 to 4 mol, per 1 mol of the compound represented by formula (11).

Examples of the catalyst for use in the reaction of the scheme F1 or F2 include palladium catalysts such as $PdCl_2$ (dppf), $Pd(PPh_3)_4$, $Pd(PPh_3)_2Cl_2$, $Pd(dba)_2$, $Pd_2(dba)_3$, $Pd(P-t-Bu_3)_2$, and $Pd(OAc)_2$.

The solvent to be used in the above reaction is preferably an aprotic polar organic solvent, preferable examples of which include N,N-dimethylformamide, N,N-dimethylacetamide, N-methylpyrrolidone, 1,3-dimethyl-2-imidazolidinone, dimethyl sulfoxide, tetrahydrofuran, and dioxane. Among these solvents, preferred are N,N-dimethylformamide, N,N-dimethylacetamide, tetrahydrofuran, dioxane, and the like, from the viewpoint of ease of removal of the reaction solvent after the reaction.

The reaction temperature can normally be within the range from −50° C. to the boiling point of the solvent, and is preferably in the range of 0 to 140° C. The reaction time is normally 0.1 to 100 hours.

After the reaction is over, a post-treatment is conducted according to an ordinary method, whereby the desired fluorene derivative can be obtained.

[Charge-Transporting Substance]

The fluorine-atom-containing polymer of the present invention can be suitably used as a charge-transporting substance. In the present invention, the charge-transporting property has the same meaning as electric conductivity, and has the same meaning as hole transporting property. The charge-transporting substance may be a substance which itself has a charge-transporting property, or may be a substance which shows a charge-transporting property when used together with a dopant. A charge-transporting varnish may be a varnish which itself has a charge-transporting property, or a varnish such that a solid film obtained therefrom has a charge-transporting property.

[Charge-Transporting Varnish]

The charge-transporting varnish of the present invention contains a charge-transporting substance consisting of the above-mentioned fluorine-atom-containing polymer, a fluorine-atom-free charge-transporting substance, a dopant consisting of a heteropoly-acid, and an organic solvent.

[Fluorine-Atom-Free Charge-Transporting Substance]

Examples of the fluorine-atom-free charge-transporting substance include charge-transporting oligomers such as aniline derivatives, thiophene derivatives, and pyrrole derivatives. The molecular weight of the charge-transporting oligomer is normally 200 to 5,000. From the viewpoint of preparing a varnish giving a highly charge-transporting thin film, the molecular weight is preferably at least 300, more preferably at least 400, and further preferably at least 500. Besides, from the viewpoint of preparing a uniform varnish giving a thin film which is high in flatness, the molecular weight is preferably up to 4,000, more preferably up to 3,000, and further preferably up to 2,000.

Among the above-mentioned charge-transporting oligomers, preferred are the aniline derivatives, in consideration of the balance between the solubility of the oligomer in organic solvents and charge-transporting properties of the thin film obtained. Examples of the aniline derivatives include the oligoaniline derivatives described in JP-A 2002-151272, the oligoaniline compounds described in WO 2004/105446, the oligoaniline compounds described in WO 2008/032617, the oligoaniline compounds described in WO 2008/032616, and the aryldiamine compounds described in WO 2013/042623.

In addition, aniline derivatives represented by the following formula (13) can also be used suitably.

[Chemical Formula 11]

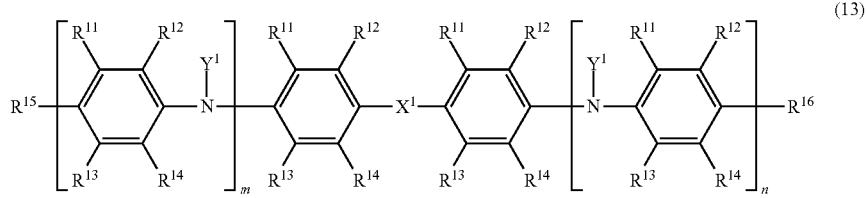

(13)

In formula (13), $X^1$ represents $-NY^1-$, $-O-$, $-S-$, $-(CR^{17}R^{18})_L-$ or a single bond, provided that it represents $-NY^1-$ when letter m or n is 0.

$Y^1$ each independently represent a hydrogen atom, a $C_1$-$C_{20}$ alkyl group, a $C_2$-$C_{20}$ alkenyl group, or a $C_2$-$C_{20}$ alkynyl group that may be substituted with $Z^{11}$, or a $C_6$-$C_{20}$ aryl group or $C_2$-$C_{20}$ heteroaryl group that may be substituted with $Z^{12}$.

Specific examples of the $C_1$-$C_{20}$ alkyl group, the $C_2$-$C_{20}$ alkenyl group, the $C_2$-$C_{20}$ alkynyl group, the $C_6$-$C_{20}$ aryl group, and the $C_2$-$C_{20}$ heteroaryl group include the same groups as above-mentioned.

$R^{17}$ and $R^{18}$ each independently represent a hydrogen atom, a chlorine atom, a bromine atom, an iodine atom, a nitro group, a cyano group, an amino group, an aldehyde group, a hydroxy group, a thiol group, a sulfonic acid group, a carboxylic acid group, a $C_1$-$C_{20}$ alkyl group, a $C_2$-$C_{20}$ alkenyl group, or a $C_2$-$C_{20}$ alkynyl group that may be substituted with $Z^{11}$, a $C_6$-$C_{20}$ aryl group or a $C_2$-$C_{20}$ heteroaryl group that may be substituted with $Z^{12}$, or $-NHY^2$, $-NY^3Y^4$, $-C(O)Y^5$, $-OY^6$, $-SY^7$, $-SO_3Y^8$, $-C(O)OY^9$, $-OC(O)Y^{10}$, $-C(O)NHY^{11}$, or $-C(O)NY^{12}Y^{13}$ group.

$Y^2$ to $Y^{13}$ each independently represent a $C_1$-$C_{20}$ alkyl group, a $C_2$-$C_{20}$ alkenyl group, or a $C_2$-$C_{20}$ alkynyl group that may be substituted with $Z^{11}$, or a $C_6$-$C_{20}$ aryl group or $C_2$-$C_{20}$ heteroaryl group that may be substituted with $Z^{12}$.

$Z^{11}$ represents a chlorine atom, a bromine atom, an iodine atom, a nitro group, a cyano group, an amino group, an aldehyde group, a hydroxy group, a thiol group, a sulfonic acid group, a carboxylic acid group, or a $C_6$-$C_{20}$ aryl group or a $C_2$-$C_{20}$ heteroaryl group that may be substituted with $Z^{13}$.

$Z^{12}$ represents a chlorine atom, a bromine atom, an iodine atom, a nitro group, a cyano group, an amino group, an aldehyde group, a hydroxy group, a thiol group, a sulfonic acid group, a carboxylic acid group, or a $C_1$-$C_{20}$ alkyl group, a $C_2$-$C_{20}$ alkenyl group, or a $C_2$-$C_{20}$ alkynyl group that may be substituted with $Z^{13}$.

$Z^{13}$ represents a chlorine atom, a bromine atom, an iodine atom, a nitro group, a cyano group, an amino group, an aldehyde group, a hydroxy group, a thiol group, a sulfonic acid group, or a carboxylic acid group.

Examples of the alkyl group, alkenyl group, alkynyl group, aryl group, and heteroaryl group of $R^{17}$, $R^{18}$, and $Y^2$ to $Y^{13}$ include the same groups as the above-mentioned ones.

Among these groups, preferred as $R^{17}$ and $R^{18}$ are the hydrogen atom and the $C_1$-$C_{20}$ alkyl groups that may be substituted with $Z^{11}$, more preferred are the hydrogen atom and a methyl group substituted with $Z^{11}$, and most preferred is the hydrogen atom.

letter L represents the number of the groups represented by $-(CR^{17}R^{18})-$, and is an integer of 1 to 20, preferably 1 to 10, more preferably 1 to 5, further preferably 1 to 2, and most preferably 1. Note that L is at least 2, the plurality of $R^{17}$ may be identical or different with each other, and the plurality of $R^{18}$ may be identical or different with each other.

Among others, $X^1$ is preferably $-NY^1-$ or a single bond. In addition, $Y^1$ is preferably a hydrogen atom or a $C_1$-$C_{20}$ alkyl group that may be substituted with $Z^{11}$, more preferably the hydrogen atom or a methyl group that may be substituted with $Z^{11}$, and most preferably the hydrogen atom.

In formula (13), $R^{11}$ to $R^{16}$ each independently represent a hydrogen atom, a chlorine atom, a bromine atom, an iodine atom, a nitro group, a cyano group, an amino group, an aldehyde group, a hydroxy group, a thiol group, a sulfonic acid group, a carboxylic acid group, a $C_1$-$C_{20}$ alkyl group, a $C_2$-$C_{20}$ alkenyl group, or a $C_2$-$C_{20}$ alkynyl group that may be substituted with $Z^{11}$, a $C_6$-$C_{20}$ aryl group or a $C_2$-$C_{20}$ heteroaryl group that may be substituted with $Z^{12}$, or $-NHY^2$, $-NY^3Y^4$, $-C(O)Y^5$, $-OY^6$, $-SY^7$, $-SO_3Y^8$, $-C(O)OY^9$, $-OC(O)Y^{10}$, $-C(O)NHY^{11}$, or $-C(O)NY^{12}Y^{13}$ ($Y^2$ to $Y^{13}$ are the same meaning as defined above.). Examples of the alkyl group, alkenyl group, alkynyl group, aryl group, and heteroaryl group include the same groups as the above-mentioned ones.

Particularly, in formula (13), $R^{11}$ to $R^{14}$ are each preferably a hydrogen atom, a chlorine atom, a bromine atom, an iodine atom, a $C_1$-$C_{10}$ alkyl group that may be substituted with $Z^{11}$, or a $C_6$-$C_{14}$ aryl group that may be substituted with $Z^{12}$, more preferably the hydrogen atom or the $C_1$-$C_{10}$ alkyl group that may be substituted with $Z^{11}$, and, most preferably, all of $R^{11}$ to $R^{14}$ are the hydrogen atom.

In addition, $R^{15}$ and $R^{16}$ are each preferably a hydrogen atom, a chlorine atom, a bromine atom, an iodine atom, a $C_1$-$C_{10}$ alkyl group that may be substituted with $Z^{11}$, a $C_6$-$C_{14}$ aryl group that may be substituted with $Z^{12}$, or a diphenylamino group that may be substituted with $Z^{12}$ (a $-NY^3Y^4$ group wherein $Y^3$ and $Y^4$ are each a phenyl group that may be substituted with $Z^{12}$), more preferably the hydrogen atom or the diphenylamino group that may be substituted with $Z^{12}$, and, further preferably, both of $R^{15}$ and $R^{16}$ are simultaneously the hydrogen atom or the diphenylamino group.

Among these, preferred is a combination wherein $R^{11}$ to $R^{14}$ are the hydrogen atom or the $C_1$-$C_{10}$ alkyl group that may be substituted with $Z^{11}$, $R^{15}$ and $R^{16}$ are the hydrogen atom or the diphenylamino group that may be substituted with $Z^{12}$, $X^1$ is $-NY^1-$ or the single bond, and $Y^1$ is the hydrogen atom or the methyl group, and more preferred is a combination wherein $R^{11}$ to $R^{14}$ are the hydrogen atom, $R^{15}$ and $R^{16}$ are simultaneously the hydrogen atom or the diphenylamino group, and $X^1$ is $-NH-$ or the single bond.

In formula (13), letter m and letter n each independently represent an integer of at least 0, and they satisfy 1≤m+n≤20. In consideration of the balance between charge-transporting properties of the thin film obtained and solubility of the aniline derivative, it is preferable that m and n satisfy 2≤m+n≤8, more preferably 2≤m+n≤6, and further preferably 2≤m+n≤4.

Especially, in $Y^1$ to $Y^{13}$ and $R^{11}$ to $R^{18}$, $Z^{11}$ is preferably a chlorine atom, a bromine atom, an iodine atom, or a $C_6$-$C_{20}$ aryl group that may be substituted with $Z^{13}$, more preferably a phenyl group that may be substituted with $Z^{13}$, and most preferably absent (in other words, non-substitution with $Z^{11}$).

$Z^{11}$ is preferably a chlorine atom, a bromine atom, an iodine atom, or a $C_1$-$C_{20}$ alkyl group that may be substituted with $Z^{13}$, more preferably a $C_3$-$C_4$ alkyl group that may be substituted with $Z^{13}$, and most preferably absent (in other words, non-substitution with $Z^{12}$).

$Z^{13}$ is preferably a chlorine atom, a bromine atom, or an iodine atom, and most preferably absent (in other words, non-substitution with $Z^{13}$).

In $Y^1$ to $Y^{13}$ and $R^{11}$ to $R^{18}$, the numbers of carbon atoms of the alkyl group, alkenyl group, and alkynyl group are preferably up to 10, more preferably up to 6, and further preferably up to 4. Besides, the numbers of carbon atoms of the aryl group and heteroaryl group are preferably up to 14, more preferably up to 10, and further preferably up to 6.

Note that the method for synthesizing the aniline derivative is not specifically restricted, and examples of the synthesizing method include the methods described in Bulletin of Chemical Society of Japan, 67, pp. 1749-1752 (1994), Synthetic Metals, 84, pp. 119-120 (1997), Thin Solid Films, 520 (24), pp. 7157-7163 (2012), WO 2008/032617, WO 2008/032616, WO 2008/129947, and WO 2013/084664.

Specific examples of the aniline derivative represented by formula (13) include, but are not limited to, those represented by the following formulas. Note that in the following formulas, DPA represents a diphenylamino group, Ph represents a phenyl group, and TPA represents a p-(diphenylamino)phenyl group.

[Chemical Formula 12]

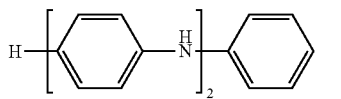
(a)

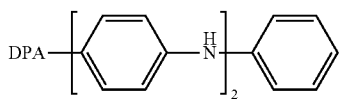
(b)

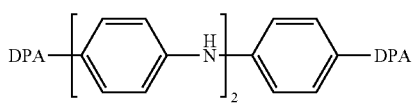
(c)

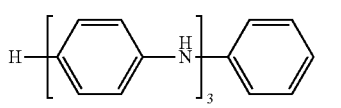
(d)

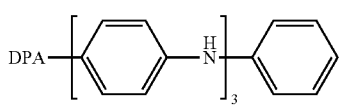
(e)

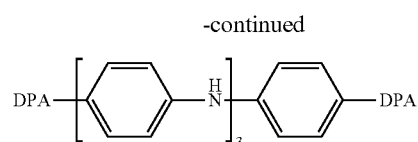
(f)

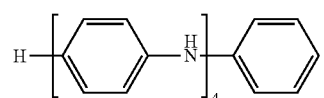
(g)

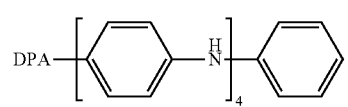
(h)

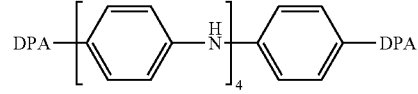
(i)

[Chemical Formula 13]

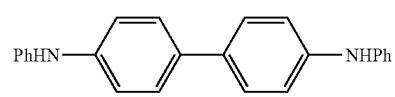
(j)

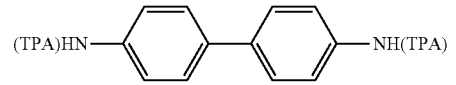
(k)

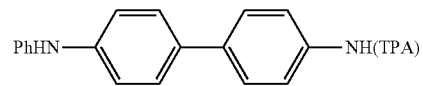
(l)

The content of the charge-transporting substance in the varnish of the present invention is preferably approximately 0.1 to 20% by weight, based on the varnish, from the viewpoint of inhibition of precipitation of the charge-transporting substance. Besides, the ratio between the amounts to be used of the charge-transporting substance composed of the fluorine-atom-containing polymer and the fluorine-atom-free charge-transporting substance, in mass ratio, is preferably such that the amount of the charge-transporting substance consisting of the fluorine-atom-containing polymer is approximately 0.1 to 5 parts, more preferably approximately 0.5 to 3 parts, and further preferably 0.5 to 1 part, per 1 part of the fluorine-atom-free charge-transporting substance, in consideration of enhancement of luminance characteristics of an organic EL element obtained.

[Dopant]

The charge-transporting varnish of the present invention contains a heteropoly-acid as a dopant. From the charge-transporting varnish, therefore, a thin film can be obtained which is excellent in charge-transporting properties such as to exhibit not only a high ability to accept holes from a transparent electrode represented by indium tin oxide (ITO) and indium zinc oxide (IZO) but also a high ability to accept holes from a metallic anode represented by aluminum.

A heteropoly-acid is a polyacid which has a structure having a hetero atom in the center of the molecule, as typically shown in a chemical structure of the Keggin type represented by the formula of Fig. 1(A1) or of the Dawson type represented by the formula of Fig. 1(A2), and in which an isopoly acid as an oxoacid of vanadium (V), molybdenum (Mo), or tungsten (W) is condensed with an oxoacid of a different element. Examples of such an oxoacid of a different element include mainly oxoacids of silicon (Si), phosphorus (P), and arsenic (As).

Specific examples of the heteropoly-acid include phosphomolybdic acid, silicomolybdic acid, phosphotungstic acid, silicotungstic acid, and phosphotungstomolybdic acid. These may be used either singly or in combination of at least two of them. Note that the heteropoly-acid for use in the present invention are commercially available, and can also be synthesized by a known method.

Particularly, where the dopant consists of one kind of heteropoly-acid, the heteropoly-acid is preferably phosphotungstic acid or phosphomolybdic acid, more preferably phosphotungstic acid. Besides, where the dopant consists of at least two kinds of heteropoly-acids, at least one of the at least two heteropoly-acids is preferably phosphotungstic acid or phosphomolybdic acid, more preferably phosphotungstic acid.

Note that even where a heteropoly-acid has a large or small number of a constituent element as compared with that in the structure represented by a general formula, as a result of quantitative analysis such as elemental analysis, the heteropoly-acid can be used in the present invention so long as the heteropoly-acid is obtained as a commercial product or has been appropriately synthesized according to a known synthesizing method.

Specifically, for example, phosphotungstic acid is generally represented by a chemical formula $H_3(PW_{12}O_{40}) \cdot nH_2O$, and phosphomolybdic acid by a chemical formula $H_3(PMo_{12}O_{40}) \cdot nH_2O$. Even where phosphotungstic acid or phosphomolybdic acid is found as a result of quantitative analysis to contain a large or small number of P (phosphorus), O (oxygen) or W (tungsten), or Mo (molybdenum) atoms as compared to that in the relevant chemical formula, the phosphotungstic acid or phosphomolybdic acid can be used in the present invention so long as it is obtained as a commercial product or has been appropriately synthesized according to a known synthesizing method. In this case, the weight of the heteropoly-acid prescribed in the present invention does not mean the pure phosphotungstic acid weight (phosphotungstic acid content) in the synthesized product or commercial product, but means the total weight of the acid inclusive of hydration water and other impurities and the like, in the state in which the acid is available as a commercial product and in the state of being isolatable in a known synthesizing method.

The amount to be used of the heteropoly-acid contained in the charge-transporting varnish of the present invention, in mass ratio, is preferably approximately 2 to 10 parts, more preferably approximately 2.5 to 9.0 parts, per 1 part of the fluorine-atom-free charging transporting substance, in consideration of obtaining with good reproducibility a charge-transporting thin film which gives a high luminance when used in an organic EL element.

[Organic Solvent]

As the organic solvent for use in preparing the charge-transporting varnish, there can be used a high-solvency solvent in which the charge-transporting substance and the dopant are well soluble.

Examples of such a high-solvency solvent include, but are not limited to, cyclohexane, N,N-dimethylformamide, N,N-dimethylacetamide, N-methylpyrrolidone, and 1,3-dimethyl-2-imidazolidinone. These solvents may be used either singly or by mixing at least two of them, and the amount thereof to be used may be 5 to 100% by weight, based on the total weight of the solvents used for the varnish.

Note that the charge-transporting substance and the dopant are preferably both dissolved completely in the above-mentioned solvent.

Besides, in the present invention, the varnish may contain at least one high-viscosity organic solvent which has a viscosity of 10 to 200 mPa·s, particularly 35 to 150 mPa·s at 25° C. and has a boiling point of 50 to 300° C., particularly 150 to 250° C. at normal pressure (atmospheric pressure). The addition of such a solvent facilitates control of the viscosity of the varnish, making it possible to prepare a varnish which gives a highly flat thin film with good reproducibility and which is suited to the applying method (coating method) to be used.

Examples of the high-viscosity organic solvent include, but are not limited to, cyclohexanol, ethylene glycol, ethylene glycol diglycidyl ether, 1,3-octylene glycol, diethylene glycol, dipropylene glycol, triethylene glycol, tripropylene glycol, 1,3-butanediol, 2,3-butanediol, 1,4-butanediol, propylene glycol, and hexylene glycol.

The ratio of addition of the high-viscosity organic solvent to the solvent used in the varnish of the present invention is preferable within such a range as not to cause precipitation of solids, and is preferably 5 to 90% by weight, provided that solid precipitation does not occur.

Further, other solvent or solvents may be mixed into the varnish in an amount of 1 to 90% by weight, preferably 1 to 50% by weight, based on the total amount of solvents used in the varnish, for the purpose of enhancing wettability of the varnish on a substrate, controlling the surface tension of the solvent, control of polarity, and control of boiling point.

Examples of such other solvent include, but are not limited to, propylene glycol monomethyl ether, ethylene glycol monobutyl ether, diethylene glycol diethyl ether, diethylene glycol monomethyl ether, diethylene glycol dimethyl ether, diethylene glycol monoethyl ether acetate, diethylene glycol monobutyl ether acetate, dipropylene glycol monomethyl ether, propylene glycol monomethyl ether acetate, diethylene glycol monoethyl ether, diacetone alcohol, γ-butyrolactone, ethyl lactate, and n-hexyl acetate. These solvents may be used either singly or by mixing at least two of them.

The viscosity of the varnish of the present invention is appropriately set according to the thickness of a thin film to be produced and according to the solids concentration, and is normally 1 to 50 mPa·s at 25° C. In addition, the solids concentration of the charge-transporting varnish in the present invention is appropriately set taking into account the viscosity and surface tension of the varnish and the thickness of the thin film to be produced, and is normally approximately 0.1 to 10.0% by weight. In consideration of enhancing the application properties of the varnish, the solids concentration is preferably 0.5 to 5.0% by weight, more preferably 1.0 to 3.0% by weight. Note that the solids in the solids concentration means the components of the varnish exclusive of the organic solvents.

[Charge-Transporting Thin Film]

By applying the charge-transporting varnish of the present invention to a substrate, followed by baking, a charge-transporting thin film can be formed on the substrate.

Examples of the method for applying the varnish (coating with the varnish) include, but are not limited to, a dipping method, a spin coating method, a transfer printing method, a roll coating method, a brushing method, an ink jet method, a spraying method, and a slit coating method. It is preferable to control the viscosity and surface tension of the varnish according to the applying method (coating method).

In addition, in the case of using the varnish of the present invention, the baking atmosphere is not limited. Not only in the atmospheric air atmosphere but also in an inert gas such as nitrogen or in vacuum, it is possible to obtain a thin film which has a uniform formed film surface and high charge-transporting properties.

The baking temperature is appropriately set generally within the range of 100 to 260° C., taking into account the use of the thin film to be obtained, the degree of charge-transporting properties to be imparted to the thin film to be obtained. In the case where the thin film is provided between and in contact with an anode and a light-emitting layer of an organic EL element and is used as a functional single film (hole injection and transport layer), the baking temperature is preferably approximately 140 to 250° C., more preferably approximately 150 to 230° C.

Note that in performing baking, a temperature change at, at least two stages, may be provided, for the purpose of ensuring a higher uniform film forming property or permitting a reaction to proceed on the substrate. The heating may be conducted by using an appropriate apparatus, such as a hot plate or an oven, for example.

The thickness of the charge-transporting thin film is not particularly limited. Where the charge-transporting thin film is used in an organic EL element, the film thickness may be approximately 5 to 200 nm. Where the charge-transporting thin film is used as a hole injection and transport layer, the film thickness is preferably 10 to 100 nm, more preferably 20 to 50 nm, and further preferably 25 to 45 nm, in consideration of enhancing the degree of phase separation between the two kinds of charge-transporting substances used in the present invention and thereby enhancing luminance characteristics and life characteristics of the organic EL element. Examples of the method for varying the film thickness include a method in which the solids concentration of the varnish is varied, and a method in which the quantity of the liquid on a substrate at the time of application (coating) is varied.

[Organic EL Element]

Examples of the materials to be used and the production method in the case of producing an organic light-emitting diode (OLED) element by use of the charge-transporting varnish of the present invention include, but are not limited to, the followings.

An electrode substrate to be used is preferably cleaned beforehand by washing it with liquid such as a detergent, an alcohol, and pure water. For instance, an anode substrate is preferably subjected to a surface treatment such as an ultraviolet (UV) ozone treatment or an oxygen-plasma treatment immediately before use thereof. Note that such a surface treatment may not necessarily be conducted, in the case where the anode material is composed mainly of organic matter.

An example of the method of producing an OLED element having a functional single film (hole injection and transport layer) composed of a thin film obtained from the charge-transporting varnish of the present invention is as follows.

The charge-transporting varnish of the present invention is applied to an anode substrate, and is baked by the above-mentioned method, to produce a functional single film on the electrode. This assembly is introduced into a vacuum vapor deposition apparatus, in which a light-emitting layer, an electron transport layer, an electron injection layer, and a cathode metal are sequentially vapor-deposited, to produce an OLED element. A carrier block layer may be provided between arbitrary layers, for controlling a light emission area.

Examples of the anode material include transparent electrodes represented by indium tin oxide (ITO) and indium zinc oxide (IZO), preferably those which have been subjected to a planarizing treatment. Polythiophene derivatives and polyaniline derivatives which have high charge-transporting properties can also be used.

Examples of the material for forming the light-emitting layer include tris(8-quinolinolato)aluminum(III) ($Alq_3$), bis(8-quinolinolato)zinc(II) ($Znq_2$), bis(2-methyl-8-quinolinolato)(p-phenylphenolato)aluminum(III) (BAlq), and 4,4'-bis(2,2-diphenylvinyl)biphenyl (DPVBi). The light-emitting layer may be formed by co-evaporation of an electron transporting material or a hole transporting material with a light-emitting dopant.

Examples of the electron transporting material include $Alq_3$, BAlq, DPVBi, 2-(4-biphenyl)-5-(4-t-butylphenyl)-1,3,4-oxadiazole (PBD), triazole derivatives (TAZ), bathocuproine (BCP), and silole derivatives.

Examples of the light-emitting dopant include quinacridone, rubrene, coumarin 540, 4-(dicyanomethylene)-2-methyl-6-(p-dimethylaminostyryl)-4H-pyran (DCM), tris(2-phenylpyridine)iridium(III) ($Ir(ppy)_3$), and (1,10-phenanthroline)-tris(4,4,4-trifluoro-1-(2-thienyl)-butane-1,3-dionato)europium(III) ($Eu(TTA)_3phen$).

Examples of the material for forming the carrier block layer include PBD, TAZ, and BCP.

Examples of the material for forming the electron injection layer include lithium oxide ($Li_2O$), magnesium oxide (MgO), alumina ($Al_2O_3$), lithium fluoride (LiF), magnesium fluoride ($MgF_2$), strontium fluoride ($SrF_2$), Liq, Li(acac), lithium acetate, and lithium benzoate.

Examples of the cathode material include aluminum, magnesium-silver alloys, aluminum-lithium alloys, lithium, sodium, potassium, and cesium.

The method of producing a polymer light-emitting diode (PLED) element by use of the charge-transporting varnish of the present invention is not particularly limited, and examples thereof include the following.

When the operation of vacuum vapor deposition of the light-emitting layer, the electron transport layer, and the electron injection layer in the production of the OLED element as above-mentioned is replaced by formation of a light-emitting polymer layer, it is possible to produce a PLED element having a functional single film (hole injection and transport layer) composed of a thin film obtained from the charge-transporting varnish of the present invention. Specifically, the charge-transporting varnish of the present invention is applied to an anode substrate, to produce a functional single film by the above-mentioned method, then a light-emitting polymer layer is formed thereon, and further a cathode electrode is vapor deposited, to produce a PLED element.

As the cathode and anode materials, similar materials to those used in producing the OLED element as above-described can be used, which can be subjected to a cleaning treatment and a surface treatment similarly to the above-mentioned.

As the method for forming the light-emitting polymer layer, there may be mentioned a method in which a solvent is added to a light-emitting polymer material or its admixture with a dopant to dissolve or uniformly disperse the polymer material and the dopant, then the resulting liquid is applied to a functional single film, and is baked to form a film.

Examples of the light-emitting polymer material include polyfluorene derivatives such as poly(9,9-dialkylfluorenes) (PDAF), polyphenylenevinylene derivatives such as poly(2-methoxy-5-(2'-ethylhexoxy)-1,4-phenylenevinylene)

(MEH-PPV), polythiophene derivatives such as poly(3-alkylthiophenes) (PAT), and polyvinylcarbazole (PVCz).

Examples of the solvent include toluene, xylene, and chloroform. Examples of the method for dissolution or uniform dispersing include stirring, stirring with heating, and ultrasonic dispersing.

The applying method (coating method) is not particularly limited, and examples thereof include an ink jet method, a spraying method, a dipping method, a spin coating method, a transfer printing method, a roll coating method, and a brushing method. Note that the application (coating) is preferably conducted in an inert gas such as nitrogen and argon.

Examples of the method for baking include a method of heating by an oven or hot plate in an inert gas or in vacuum.

The organic EL element of the present invention may, if necessary, be sealed together with a desiccant according to a common method, for the purpose of preventing the characteristics thereof from being worsened.

EXAMPLES

The present invention will be described more specifically below by showing Synthesis Examples, Examples, and Comparative Examples, but the present invention is not limited to the followings. Note that the apparatuses which were used are as follows.
(1) $^1$H-NMR: ECX-300, made by JEOL Ltd.
(2) LC/MS: ZQ 2000, made by Waters Corporation
(3) Substrate cleaning: Substrate cleaning apparatus (vacuum plasma system), made by Choshu Industry Co., Ltd.
(4) Application of varnish: Spin coater MS-A100, made by Mikasa Co., Ltd.
(5) Film thickness measurement: Microfigure measuring instrument Surfcorder ET-4000, made by Kosaka Laboratory Ltd.
(6) Measurement of weight average molecular weight (Mw) and number average molecular weight (Mn): made by Shimadzu Corporation (Column: SHODEX GPC KF-8031+GPC KF-804L, column temperature: 40° C., detector: UV detector (254 nm) and RI detector, eluent: THF, column flow rate: 1.0 mL/minute)
(7) Production of organic EL element: Multifunctional deposition apparatus system C-E2L1G1-N, made by Choshu Industry Co., Ltd.
(8) Measurement of luminance, etc. of organic EL element: I-V-L measurement system, made by Tech World Inc.

[1] Synthesis of Monomer

Synthesis Example 1

Synthesis of Compound 1

[Chemical Formula 15]

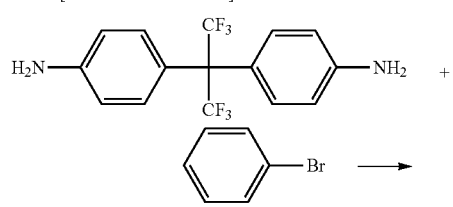

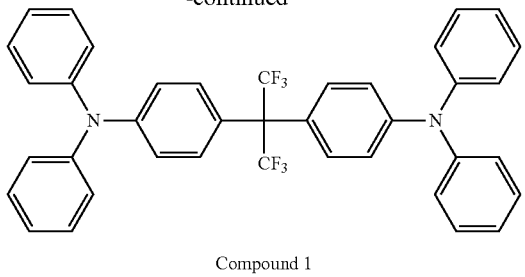

Compound 1

To 100 mL of a toluene suspension containing 5 g (15 mmol) of 4,4'-(perfluoropropane-2,2-diyl)dianiline and 11.3 g (72 mmol) of bromobenzene, were added 690 mg (1.2 mmol) of Pd(dba)$_2$, 8.65 g (90 mmol) of t-BuONa, and 696 mg (2.4 mmol) of [(t-Bu)$_3$PH]BF$_4$, followed by replacing the atmosphere with nitrogen and heating at reflux for one hour. After the reaction was over, the reaction mixture was let cool to room temperature, and 100 mL of water was added thereto, followed by extraction with ethyl acetate. The resulting organic layer was dried by use of sodium sulfate, followed by celite filtration. The filtrate was concentrated to obtain a crude product, which was purified by silica gel column chromatography (eluent: toluene), and a fraction containing Compound 1 was concentrated. 30 mL of a toluene solution of the crude product obtained was added dropwise to 250 mL of methanol, then the precipitated solid was separated by filtration, to obtain 7.88 g of Compound 1 as a light yellow solid (yield: 82%). Measurement results of $^1$H-NMR and LC/MS are given below.

$^1$H-NMR (300 MHz, CDCl$_3$): δ 6.97 (d, J=9.0 Hz, 4H), 7.04-7.14 (m, 12H), 7.20-7.31 (m, 12H).

LC/MS (ESI$^+$) m/z; 639 [M+1]$^+$

Synthesis Example 2

Synthesis of Compound 2

[Chemical Formula 16]

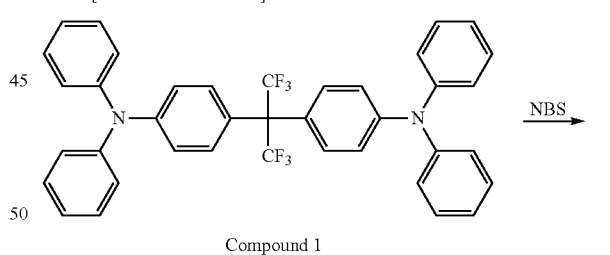

Compound 1

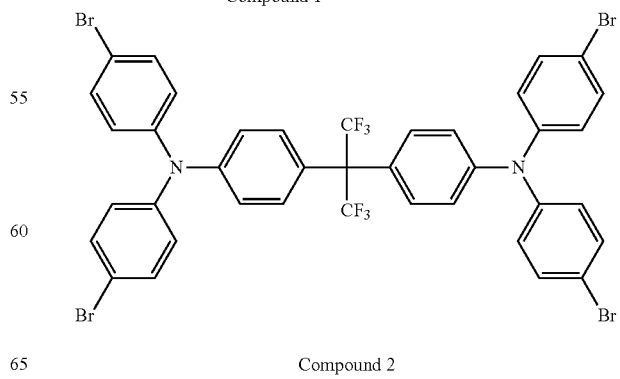

Compound 2

To 7.76 g (12.2 mmol) of Compound 1 were added 155 mL of DMF and 40 mL of THF, to obtain a solution, which was then cooled to 0° C., and 9.08 g (51 mmol) of N-bromosuccinimide was added thereto. Thereafter, the reaction mixture was stirred at room temperature for one hour, was then cooled to 0° C., and 100 mL of water was added thereto dropwise. The resulting organic layer was extracted with ethyl acetate, was dried by use of sodium sulfate, followed by filtration, and the filtrate was concentrated. 40 mL of the thus obtained THF solution as a yellow liquid was added dropwise to 400 mL of water, followed by stirring for one hour. After the stirring, the precipitated solid was separated by filtration, and was further washed with hexane, to obtain 10.3 g of Compound 2 as a colorless solid (yield: 88%). Measurement results of $^1$H-NMR and LC/MS are given below.

$^1$H-NMR (300 MHz, CDCl$_3$): δ 6.96-6.99 (m, 12H), 7.24 (d, J=9.3 Hz, 4H), 7.37-7.41 (m, 8H).

LC/MS (ESI$^+$) m/z; 953 [M+1]$^+$

Synthesis Example 3

Synthesis of Compound 3

[Chemical Formula 17]

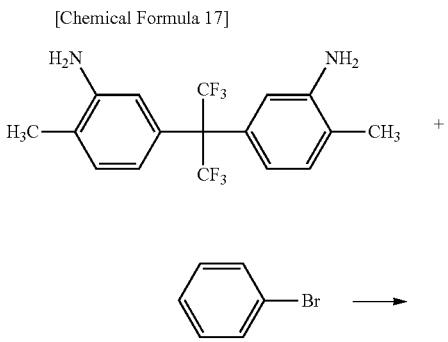

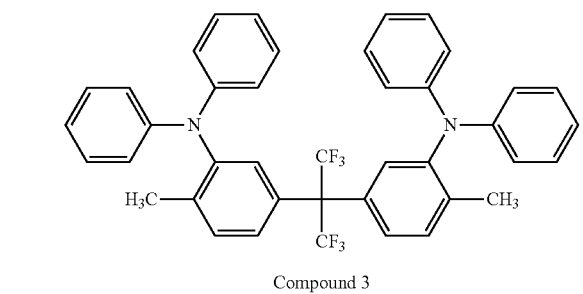

Compound 3

By similar method as in Synthesis Example 1 except for using 3,3'-(perfluoropropane-2,2-diyl)bis(6-methylaniline) in place of 4,4'-(perfluoropropane-2,2-diyl)dianiline, 25.4 g of Compound 3 was obtained as a light yellow solid (yield: 92%). Measurement results of $^1$H-NMR and LC/MS are given below.

$^1$H-NMR (300 MHz, CDCl$_3$): δ 1.98 (s, 6H), 6.86-6.93 (m, 12H), 7.08-7.19 (m, 14H).

LC/MS (ESI$^+$) m/z; 667 [M+1]$^+$

Synthesis Example 4

Synthesis of Compound 4

[Chemical Formula 18]

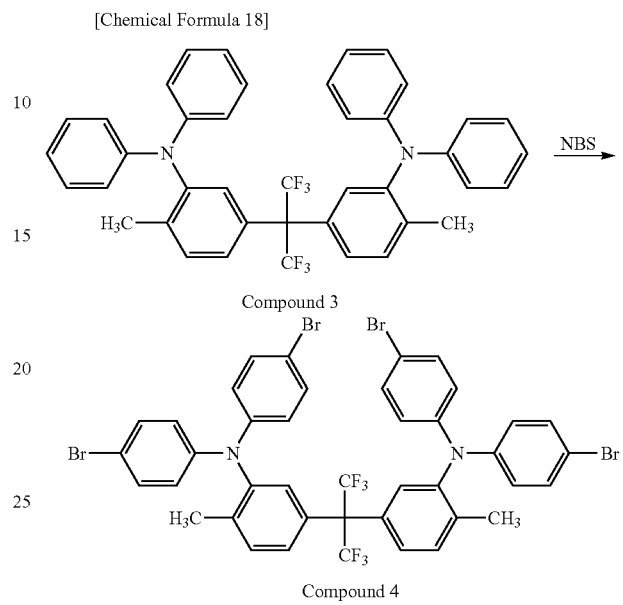

By similar method as in Synthesis Example 2 except for using Compound 3 in place of Compound 1, 2.23 g of Compound 4 was obtained as a colorless solid (yield: 76%). Measurement results of $^1$H-NMR and LC/MS are given below.

$^1$H-NMR (300 MHz, CDCl$_3$): δ 1.99 (s, 6H), 6.71-6.74 (m, 8H), 6.99 (s, 2H), 7.12-7.21 (m, 4H), 7.25-7.30 (m, 8H).

LC/MS (ESI$^+$) m/z; 983 [M+1]$^+$

Synthesis Example 5

Synthesis of Compound 5

[Chemical Formula 19]

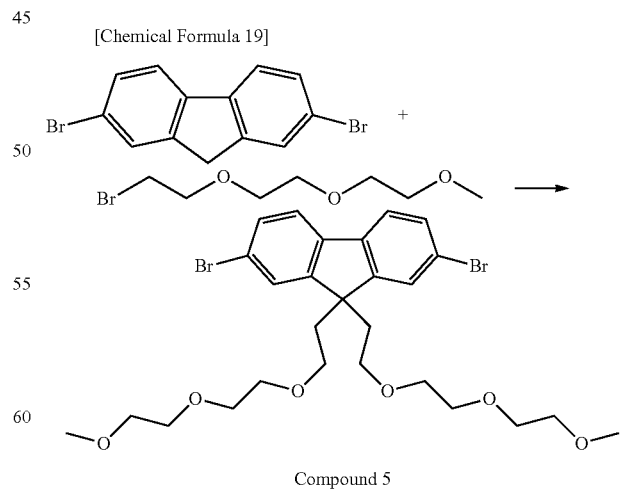

To 130 mL of a dimethyl sulfoxide suspension containing 6.48 g (20 mmol) of 2,7-dibromofluorene were added 5.61 g (100 mmol) of potassium hydroxide, 0.33 g (2 mmol) of potassium iodide, and 9.99 g (44 mmol) of diethylene glycol 2-bromoethyl methyl ether, followed by stirring at room temperature for 24 hours. After the reaction was over, the reaction mixture was cooled to 0° C., then 120 mL of water was added thereto, and neutralization with hydrochloric acid was conducted. The resulting organic layer was extracted with ethyl acetate, followed by drying by use of magnesium sulfate, and the crude product obtained upon concentration was purified by silica gel column chromatography [eluent: hexane/ethyl acetate (4/1→3/1→2/1 (v/v))], to obtain 8.30 g of Compound 5 as a yellow solid (yield: 67%). Measurement results of $^1$H-NMR and LC/MS are given below.

$^1$H-NMR (300 MHz, CDCl$_3$): δ 2.33 (app t, J=7.8 Hz, 4H), 2.78 (app t, J=7.8 Hz, 4H), 3.19-3.22 (m, 4H), 3.35 (s, 6H), 3.37-3.41 (m, 4H), 3.50-3.52 (m, 8H), 7.46 (dd, J=1.8, 8.4 Hz, 2H), 7.51 (d, J=8.4 Hz, 2H), 7.53 (d, J=1.8 Hz, 2H).

LC/MS (ESI$^+$) m/z; 634 [M+NH$_4$]$^+$

Synthesis Example 6

Synthesis of Compound 6

[Chemical Formula 20]

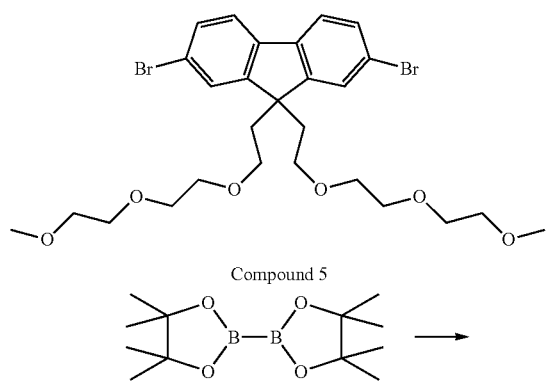

Compound 5

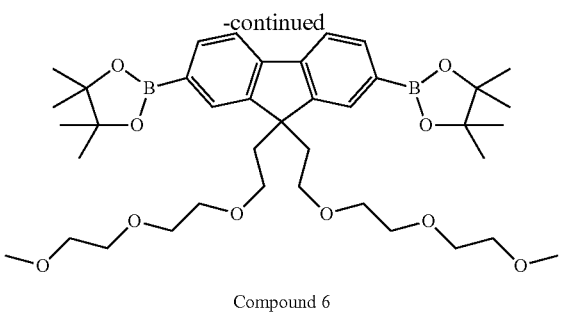

Compound 6

To 82 mL of a 1,4-dioxane solution containing 8.28 g (13.4 mmol) of Compound 5 and 7.50 g (29.6 mmol) of bis(pinacolato)diboron, were added 5.26 g (53.6 mmol) of potassium acetate and 0.44 g (0.53 mmol) of dichloromethane adduct of PdCl$_2$(dppf), followed by replacing the atmosphere with nitrogen and heating at 100° C. for two hours. After the reaction was over, the reaction mixture was subjected to celite filtration, and the filtrate was concentrated to obtain a crude product, which was purified by silica gel column chromatography [eluent: hexane/ethyl acetate (1/1→1/2 (v/v))], to obtain 7.55 g of Compound 6 as a colorless solid (yield: 79%). Measurement results of $^1$H-NMR and LC/MS are given below.

$^1$H-NMR (300 MHz, CDCl$_3$): δ 1.39 (s, 24H), 2.43 (app t, J=7.2 Hz, 4H), 2.68 (app t, J=8.1 Hz, 4H), 3.16-3.20 (m, 4H), 3.33 (s, 6H), 3.37-3.40 (m, 4H), 3.45-3.56 (m, 8H), 7.70 (d, J=7.5 Hz, 2H), 7.80 (d, J=7.5 Hz, 2H), 7.84 (s, 2H).

LC/MS (ESI$^+$) m/z; 728 [M+NH$_4$]$^+$

[2] Synthesis of Polymer

Synthesis Example 7

Synthesis of Polymer 1

[Chemical Formula 21]

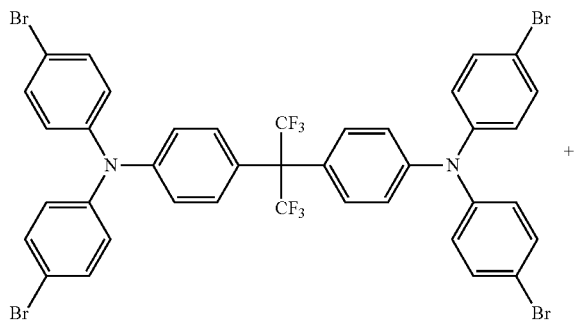

Compound 2

-continued

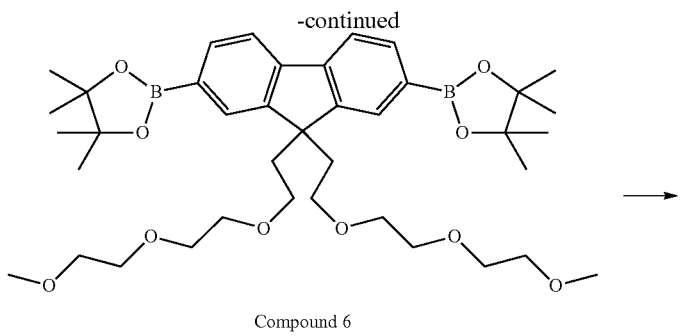

Compound 6

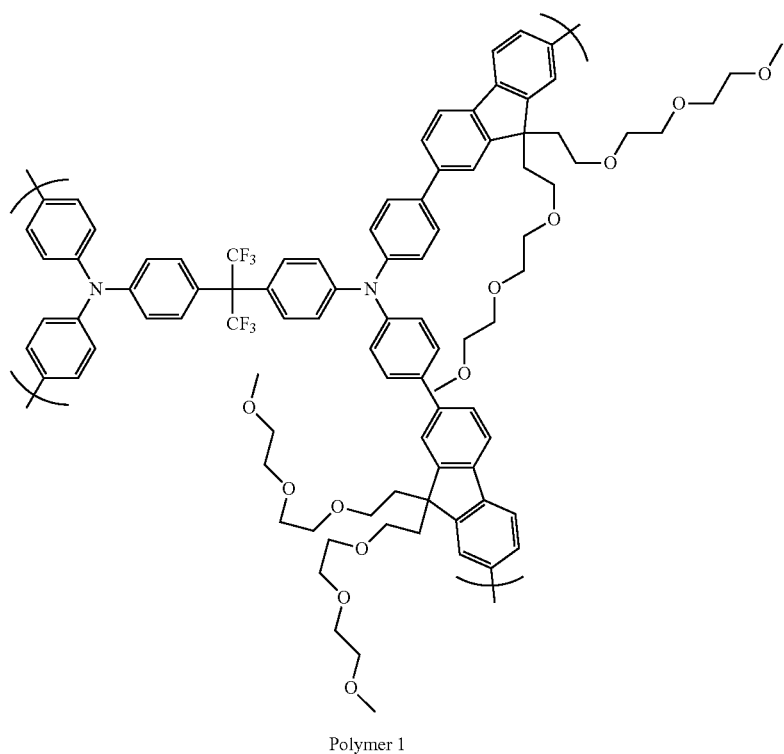

Polymer 1

To 16 mL of a toluene solution containing 804 mg (0.84 mmol) of Compound 2 and 1 g (1.4 mmol) of Compound 6, were added 67.9 mg (0.17 mmol) of methyl tri-n-octylammonium chloride, 3.9 mg (3.36 μmol) of Pd(PPh$_3$)$_4$, and 3.36 mL (6.72 mmol) of a 2 mol/L aqueous sodium carbonate solution, followed by heating at 80° C. for one hour. To the reaction mixture was added 102 mg (0.84 mmol) of phenylboronic acid, followed by further heating at 80° C. for four hours. After the reaction was over, 50 mL of toluene was added to the reaction mixture, the resulting organic layer was washed with 1 mol/L hydrochloric acid, and was dried by use of sodium sulfate. After celite filtration, the organic layer was concentrated to a volume of ¼ times the original volume, and was added dropwise to 160 mL of methanol. The resulting admixture was stirred at room temperature for three hours, after which the precipitated solid was separated by filtration. The solid was dissolved in 15 mL of toluene, the resulting solution was added dropwise to 160 mL of methanol, followed by stirring at room temperature for three hours, and then the precipitated solid was separated by filtration, to obtain 1.03 g of Polymer 1 as a light green solid. Measurement results of Mw and Mn by GPC are given below.

Mw=57,500

Mn=8,500

Mw/Mn=6.7

Synthesis Example 8
Synthesis of Polymer 2
[Chemical Formula 22]
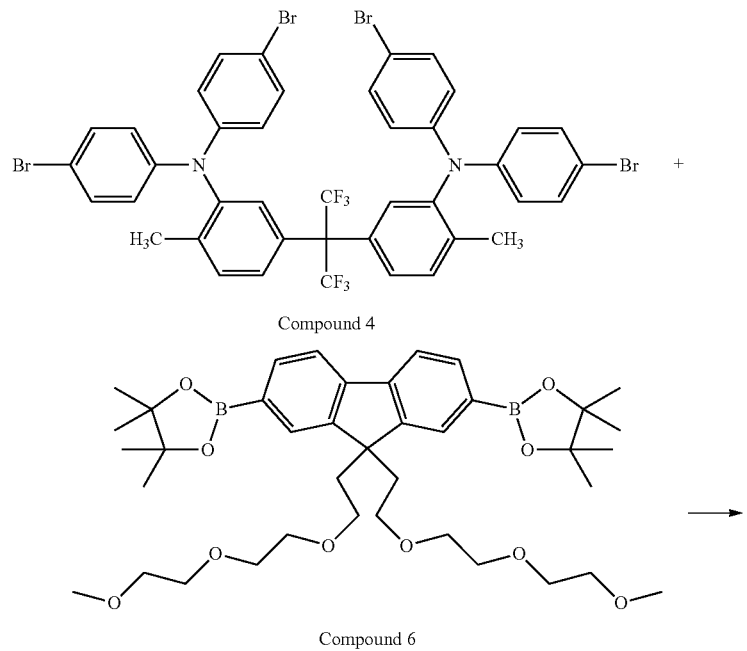
Compound 4
Compound 6
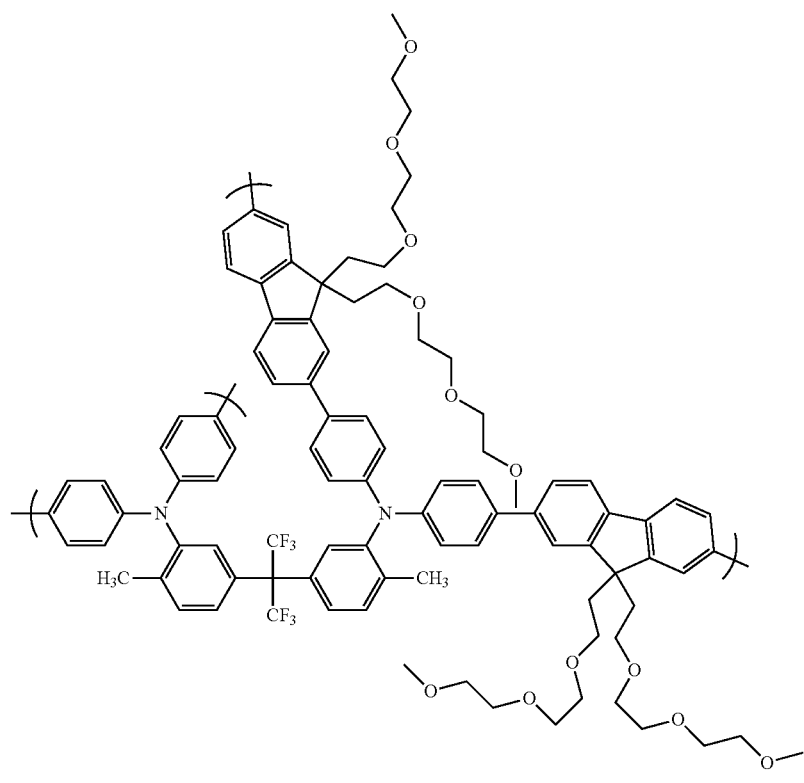
Polymer 2

By similar method as in Synthesis Example 7 except for using Compound 4 in place of Compound 2, 0.47 g of Polymer 2 was obtained as a light yellow solid. Measurement results of Mw and Mn by GPC are given below.

Mw=55,000
Mn=9,300
Mw/Mn=5.9

[3] Preparation of Charge-Transporting Varnish

Example 1

Preparation of Charge-Transporting Varnish A

To a mixture of 64 mg of Polymer 1, 18 mg of an oligoaniline compound 1 represented by the following formula, and 89 mg of phosphotungstic acid (made by Kanto Chemical Co., Inc.), was added 2 g of 1,3-dimethylimidazolidinone in a nitrogen circulation type glove box, followed by stirring with heating at 50° C., to effect dissolution. To the resulting solution was added 2 g of cyclohexanol, followed by stirring, to obtain a green solution. The solution was filtered through a syringe filter having a pore diameter of 0.2 μm, to obtain a charge-transporting varnish A. Note that the oligoaniline compound 1 was synthesized according to the method described in WO 2013/084664.

[Chemical Formula 23]

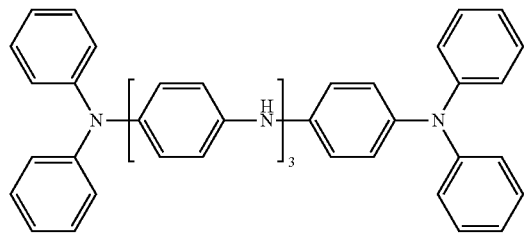

oligoaniline compound 1

Example 2

Preparation of Charge-Transporting Varnish B

To a mixture of 86 mg of Polymer 1, 14 mg of the oligoaniline compound 1, and 72 mg of phosphotungstic acid (made by Kanto Chemical Co., Inc.), was added 2 g of 1,3-dimethylimidazolidinone in a nitrogen circulation type glove box, followed by stirring with heating at 50° C., to effect dissolution. To the resulting solution was added 2 g of cyclohexanol, followed by stirring, to obtain a green solution. The solution was filtered through a syringe filter having a pore diameter of 0.2 μm, to obtain a charge-transporting varnish B.

Example 3

Preparation of Charge-Transporting Varnish C

To a mixture of 64 mg of Polymer 2, 18 mg of the oligoaniline compound 1, and 89 mg of phosphotungstic acid (made by Kanto Chemical Co., Inc.), was added 2 g of 1,3-dimethylimidazolidinone in a nitrogen circulation type glove box, followed by stirring with heating at 50° C., to effect dissolution. To the resulting solution was added 2 g of cyclohexanol, followed by stirring, to obtain a green solution. The solution was filtered through a syringe filter having a pore diameter of 0.2 μm, to obtain a charge-transporting varnish C.

Comparative Example 1

Preparation of Charge-Transporting Varnish D

By similar method as in Example 1 except that Polymer 1 was not used and the oligoaniline compound 1 and phosphotungstic acid were used in respective amounts of 20 mg and 100 mg, a charge-transporting varnish D was prepared.

[4] Production and Characteristics Evaluation of Organic EL Element (OLED Element)

As a substrate at the time of evaluating electrical characteristics, a 25 mm×25 mm×0.7 (t) glass substrate provided on its surface with a pattern of indium tin oxide in a thickness of 150 nm (hereinafter referred to simply as ITO substrate) was used. The ITO substrate was used after impurities on the surface thereof were removed by an $O_2$ plasma cleaning apparatus (150 W, 30 seconds).

Example 4

Production of OLED Element by Use of Charge-Transporting Varnish A

The charge-transporting varnish A obtained in Example 1 was applied to the ITO substrate by use of a spin coater, followed by drying at 80° C. for one minute and, further, baking at 230° C. for 15 minutes, to form a 30 nm-thick uniform thin film on the ITO substrate.

Next, thin films of tris(8-quinolinolato)aluminum(III) ($Alq_3$), lithium fluoride, and aluminum were subsequently layered over the ITO substrate (having been provided thereon with the thin film) by use of a vapor deposition apparatus (vacuum degree $1.0 \times 10^{-5}$ Pa), to obtain an OLED element. In this case, the vapor deposition rate was 0.2 nm/second for $Alq_3$ and aluminum, and 0.02 nm/second for lithium fluoride. The thicknesses of the thin films were 40 nm, 0.5 nm, and 100 nm, respectively.

Note that for preventing characteristics of the OLED element from being deteriorated under the influence of oxygen, moisture and the like in air, the OLED element was sealed by use of sealing substrates, before evaluation of the characteristics. The sealing was conducted according to the following procedure.

In a nitrogen atmosphere having an oxygen concentration of up to 2 ppm and a dew point of up to −85° C., the organic EL element was placed between the sealing substrates, and the sealing substrates were laminated together using an adhesive (XNR5516Z-B1, made by Nagase Chemtex Corporation). In this case, a desiccant (HD-071010W-40, made by Dynic Corporation) was placed together with the OLED element inside the sealing substrates. The adhesive was cured by irradiating the laminated sealing substrates with UV light (wavelength: 365 nm, dosage: 6,000 mJ/cm$^2$), and annealing at 80° C. for one hour.

Example 5

Production of OLED Element by Use of Charge-Transporting Varnish B

An OLED element was produced by similar method as in Example 4, except that the charge-transporting varnish B obtained in Example 2 was used in place of the charge-transporting varnish A.

Example 6

Production of OLED Element by Use of Charge-Transporting Varnish C

An OLED element was produced by similar method as in Example 4, except that the charge-transporting varnish C obtained in Example 3 was used in place of the charge-transporting varnish A.

Comparative Example 2

Production of OLED Element by Use of Charge-Transporting Varnish D

An OLED element was produced by similar method as in Example 4, except that the charge-transporting varnish D obtained in Comparative Example 1 was used in place of the charge-transporting varnish A.

The OLED elements obtained in Examples 4 to 6 and Comparative Example 2 were put to measurements of electrical characteristics. Current density, luminance, and current efficiency at a driving voltage of 5 V are set forth in Table 1.

TABLE 1

| | Current density (mA/cm$^2$) | Luminance (cd/m$^2$) | Current efficiency (cd/A) |
|---|---|---|---|
| Example 4 | 54 | 1,270 | 2.4 |
| Example 5 | 35 | 662 | 2.6 |
| Example 6 | 84 | 1,925 | 2.3 |
| Comparative Example 2 | 3,425 | 611 | 0.0 |

As shown in Table 1, it was seen that in Comparative Example 2 wherein the charge-transporting varnish containing neither of Polymers 1 and 2 was used, the current efficiency was conspicuously low, and the luminance was low in relation to the current density, as compared to Examples 4 to 6 wherein the charge-transporting varnishes A to C containing Polymer 1 or 2 were used.

Thus, it is seen that by use of the charge-transporting varnish of the present invention, it is possible to produce a thin film capable of exhibiting excellent luminance characteristics when used for an organic EL element.

The invention claimed is:

1. A fluorine-atom-containing polymer that is a condensation polymer of a fluorine-atom-containing triphenylamine derivative giving a repeating unit represented by formula (1) and a fluorene derivative giving a repeating unit represented by formula (2):

[Chemical Formula 1]

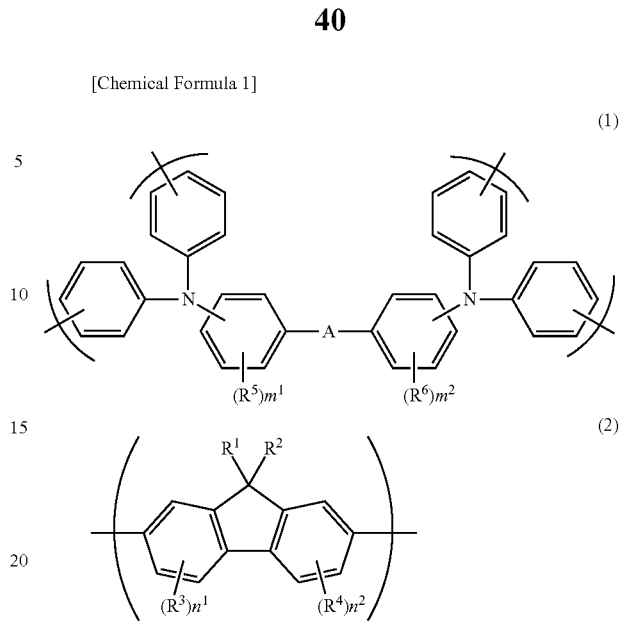

wherein A represents a $C_1$-$C_6$ fluoroalkanediyl group;
$R^1$ and $R^2$ each independently represent a hydrogen atom, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_2$-$C_{20}$ heteroaryl group, a $C_1$-$C_{20}$ alkoxy group, a $C_2$-$C_{20}$ alkenyloxy group, a $C_2$-$C_{20}$ alkynyloxy group, a $C_6$-$C_{20}$ aryloxy group, a $C_2$-$C_{20}$ heteroaryloxy group, or a $C_2$-$C_{20}$ alkyl group including at least one ether structure (provided that at least one of $R^1$ and $R^2$ represents any of the alkyoxy group, the alkenyloxy group, the alkynyloxy group, the aryloxy group, the heteroaryloxy group, and the alkyl group including at least one ether structure);
$R^3$ to $R^6$ each independently represent a halogen atom, a nitro group, a cyano group, a $C_1$-$C_{20}$ alkyl group, a $C_2$-$C_{20}$ alkenyl group, a $C_2$-$C_{20}$ alkynyl group, a $C_1$-$C_{20}$ alkoxy group, a $C_2$-$C_{20}$ alkenyloxy group, or a $C_2$-$C_{20}$ alkynyloxy group that may be substituted with $Z^1$, or a $C_6$-$C_{20}$ aryl group, a $C_2$-$C_{20}$ heteroaryl group, a $C_6$-$C_{20}$ aryloxy group, or a $C_2$-$C_{20}$ heteroaryloxy group that may be substituted with $Z^2$, and respective $R^3$ to $R^6$ may be identical or different with each other;
$Z^1$ represents a halogen atom, a nitro group, a cyano group, or a $C_6$-$C_{20}$ aryl group, a $C_2$-$C_{20}$ heteroaryl group, a $C_1$-$C_{20}$ alkoxy group, or a $C_2$-$C_{20}$ alkenyloxy group, or a $C_2$-$C_{20}$ alkynyloxy group, that may be substituted with $Z^3$;
$Z^2$ represents a halogen atom, a nitro group, a cyano group, or a $C_1$-$C_{20}$ alkyl group, a $C_2$-$C_{20}$ alkenyl group, a $C_2$-$C_{20}$ alkynyl group, a $C_1$-$C_{20}$ alkoxy group, a $C_2$-$C_{20}$ alkenyloxy group, a $C_2$-$C_{20}$ alkynyloxy group, a $C_6$-$C_{20}$ aryl group, or a $C_2$-$C_{20}$ heteroaryl group that may be substituted with $Z^3$;
$Z^3$ represents a halogen atom, a nitro group, or a cyano group;
letters $m^1$ and $m^2$ respectively represent the numbers of substituents $R^5$ and $R^6$, and each independently represent an integer of 0 to 4; and
letters $n^1$ and $n^2$ respectively represent the numbers of substituents $R^3$ and $R^4$, and each independently represent an integer of 0 to 3.

2. The polymer according to claim 1, wherein the polymer has a weight average molecular weight of 1,000 to 200,000.

3. The polymer according to claim 1 or 2, wherein A is
a perfluoromethanediyl group, a perfluoroethane-1,2-diyl group, a perfluoropropane-1,3-diyl group,
a perfluoropropane-2,2-diyl group,
a perfluorobutane-1,4-diyl group,
a perfluoropentane-1,5-diyl group, or
a perfluorohexane-1,6-diyl group.

4. The polymer according to claim 1, wherein both of $R^1$ and $R^2$ are an alkoxy group, an alkenyloxy group, an alkynyloxy group, an aryloxy group, a heteroaryloxy group, or an alkyl group including at least one ether structure.

5. A charge-transporting substance consisting of the polymer according to claim 1.

6. A charge-transporting varnish comprising the charge-transporting substance according to claim 5, a fluorine-atom-free charge-transporting substance, a dopant consisting of a heteropoly-acid, and an organic solvent.

7. The charge-transporting varnish according to claim 6, wherein the fluorine-atom-free charge-transporting substance is an aniline derivative.

8. A charge-transporting thin film produced by use of the charge-transporting varnish according to claim 6 or 7.

9. An electronic device comprising the charge-transporting thin film according to claim 8.

10. An organic electroluminescent element comprising the charge-transporting thin film according to claim 8.

11. A method of producing a charge-transporting thin film comprising applying the charge-transporting varnish according to claim 6 or 7 to a substrate, and evaporating off the solvent.

* * * * *